(12) United States Patent
Fackelman et al.

(10) Patent No.: US 10,586,621 B2
(45) Date of Patent: Mar. 10, 2020

(54) VALIDATING AND VISUALIZING PERFORMANCE OF ANALYTICS

(71) Applicant: International Business Machines Corporation, Armonk, NY (US)

(72) Inventors: Robert M. Fackelman, Cleveland, OH (US); Mark E. Modic, Brecksville, OH (US); Matthew Orcutt, Chagrin Falls, OH (US); Rachel A. Scagnetti, Cleveland, OH (US)

(73) Assignee: International Business Machines Corporation, Armonk, NY (US)

( * ) Notice: Subject to any disclaimer, the term of this patent is extended or adjusted under 35 U.S.C. 154(b) by 526 days.

(21) Appl. No.: 15/150,653

(22) Filed: May 10, 2016

(65) Prior Publication Data

US 2017/0329813 A1    Nov. 16, 2017

(51) Int. Cl.
*G16H 50/70* (2018.01)
*G06F 19/00* (2018.01)

(52) U.S. Cl.
CPC ............ *G16H 50/70* (2018.01); *G06F 19/00* (2013.01)

(58) Field of Classification Search
None
See application file for complete search history.

(56) References Cited

U.S. PATENT DOCUMENTS

| | | | |
|---|---|---|---|
| 2001/0039503 A1 | 11/2001 | Chan et al. | |
| 2003/0115083 A1* | 6/2003 | Masarie, Jr. | ........... G16H 15/00 705/2 |
| 2007/0055653 A1 | 3/2007 | Guerra Currie et al. | |
| 2008/0209392 A1* | 8/2008 | Able | ........................ G06F 8/34 717/105 |
| 2011/0191343 A1* | 8/2011 | Heaton | ................... G06F 19/00 707/737 |
| 2013/0124523 A1* | 5/2013 | Rogers | .................... G06F 19/32 707/737 |
| 2014/0032240 A1 | 1/2014 | Lougheed et al. | |

(Continued)

OTHER PUBLICATIONS

"The Explorys Platform", IBM Watson Health, Solution Brief, Produced in the United States of America, Nov. 2015, 4 pages.

(Continued)

*Primary Examiner* — Matthew J Ellis
(74) *Attorney, Agent, or Firm* — Ryan Lewis; Edell, Shapiro & Finnan, LLC

(57) ABSTRACT

According to one embodiment of the present invention, a system detects conditions for analytics and includes at least one processor. The system analyzes a structured document including a plurality of sections each specifying a set of conditions for members of a population in a structured format. The structured document is utilized to perform an analytic on the population. Each section within the structured document is identified and a corresponding set of conditions for that identified section in the structured format is extracted. The corresponding extracted set of conditions for each section is translated to an unstructured format for visual presentation of each identified section with a description of the corresponding set of conditions. Embodiments of the present invention further include a method and computer program product for detecting conditions for analytics in substantially the same manner described above.

17 Claims, 27 Drawing Sheets

(56) References Cited

U.S. PATENT DOCUMENTS

| | | | |
|---|---|---|---|
| 2014/0365210 A1 | 12/2014 | Riskin et al. | |
| 2015/0112700 A1* | 4/2015 | Sublett | G06Q 10/06393 |
| | | | 705/2 |
| 2016/0019356 A1* | 1/2016 | Martin | G06F 19/324 |
| | | | 705/2 |
| 2016/0267223 A1* | 9/2016 | Allen | G16H 10/60 |

OTHER PUBLICATIONS

"Evidence Analysis and Presentation to Indicate Reasons for Membership in Populations", U.S. Appl. No. 15/064,071, filed Mar. 8, 2016, 46 pages.

* cited by examiner

740
```
<DenominatorDescription>All patients aged 6 months and older seen for at least two visits or at least
one preventive visit during the measurement period</DenominatorDescription> ——742

<NumeratorDescription>Patients who have received an influenza immunization OR who reported
previous receipt of influenza immunization </NumeratorDescription>
                                    ——744

<ExclusionDescription> </ExclusionDescription> ——746

<ExceptionDexcription>Documentation of medical/patient/system reason(s) for not receiving an
influenza immunization during the flu season</ExceptionDexcription> ——748
```

710
```
<description>Percentage of patients aged 6 months and older seen for a visit between START
MM/DD/YYYY and END MM/DD/YYYY who received an influenza immunization between START
MM/DD/YYYY and END MM/DD/YYYY. </description>
```

725 / 720
```
<defaultTarget>
    <targetScore>48.29</targetScore>
    <targetUnit>PERCENT</targetUnit>
    <targetDesire>ABOVEOREQUAL</targetDesire>
    <targetSource>MSSP YYYY/YYYY (50th percentile)</targetSource>
</defaultTarget>
```

730
```
<basePeriod durationUnit="MONTHS" duration="12" xml:id="reporting.period"/> ——732

<everPeriod xml:id="reporting.period.ever"/> ——734

<absolutePeriod xml:id="absolute.period.visit" attenuateToReferenceDate="true" endDay="DD"
endMonth="MM" endYear="YYYY" startDay="DD" startMonth="MM" startYear="YYYY"/>
                                    ——736
<absolutePeriod xml:id="absolute.period.fluseason" attenuateToReferenceDate="true"
endDay="DD" endMonth="MM" endYear="YYYY" startDay="DD" startMonth="MM"
startYear="YYYY"/>                  ——738
```

FIG.7

910 —<denominator>
                915 —<cohort>
                    920 —<age unit="MONTHS" periodQual="ON_START_DATE" period="reporting.period" max="" min="0"/>
                    <or>
                        <daysGroup minDays="2" description="Outpatient encounter(Office visit)">
                            <encounter type="OFFICE_VISIT"/>
                            <encounter type="OUTPATIENT"/>
                            <procedure cptCodes="99201"/>
                            <procedure cptCodes="99202"/>
                            <procedure cptCodes="99203"/>
                            <procedure cptCodes="99212"/>
                            <procedure cptCodes="99213"/>
                            <procedure cptCodes="99214"/>
                            <procedure cptCodes="99215"/>
                            <procedure cptCodes="99241"/>
                            <procedure cptCodes="99307"/>
                            <procedure cptCodes="99308"/>
                            <procedure cptCodes="99315"/>
                            <procedure cptCodes="99316"/>
                            <procedure cptCodes="99324"/>
                            <procedure cptCodes="99325"/>
                            <procedure cptCodes="99326"/>
                            <procedure cptCodes="99327"/>
                            <procedure cptCodes="99328"/>
                        </daysGroup>
                        930 —<or description="Preventive visit">
                            <procedure cptCodes="99385"/>
                            <procedure cptCodes="99386"/>
                            <procedure cptCodes="99387"/>
                            <procedure cptCodes="99391"/>
                            <procedure cptCodes="99412"/>
                            <procedure cptCodes="99429"/>
                            <procedure cptCodes="G0438"/>
                            <procedure cptCodes="G0439"/>
                        </or>
                    </or>
                    <or period="absolute.period.visit" description="Outpatient encounter(Office visit)"> — 960
                </cohort>—915
910 —</denominator>

FIG.9

```
-<numerator>
 -<cohort>
  -<temporalSequence uniqueResults="true">
    <index>
      <firstDate>
        -<or description="PHQ-9 assessment" period="reporting.period.index">              1110
           <observation min="9" loincTests="44249-1"/>
           <observation min="9" loincTests="44257-4"/>
           <observation min="9" loincTests="44261-6"/>
           <observation min="9" loincTests="54635-8"/>
        </or>                                                 1115
      </firstDate>
    </index>
         <targetEvent max="395" min="335" maxunits="DAYS" minunits="DAYS">     1120
         -<or description="PHQ-9 assessment" period="reporting.period.ever">
           <observation max="5" loincTests="44249-1" which="LAST"/>
           <observation max="5" loincTests="44257-4" which="LAST"/>
           <observation max="5" loincTests="44261-6" which="LAST"/>
           <observation max="5" loincTests="54635-8" which="LAST"/>
         </or>
         </targetEvent>
  </temporalSequence>
 </cohort>
</numerator>
```

```
<linkFilters>                                                    ─ 1312
  <filter name="Outpatient">
    <encounterLink linkType="ENCOUNTER">
      <or description="Outpatient encounter(Office visit)">
        <encounter type="OUTPATIENT"/>
        <encounter type="OFFICE_VISIT"/>
        <procedure cptCodes="99201"/>
        <procedure cptCodes="99202"/>
        <procedure cptCodes="99203"/>
        <procedure cptCodes="99204"/>
        <procedure cptCodes="99205"/>
        <procedure cptCodes="99212"/>
        <procedure cptCodes="99213"/>
        <procedure cptCodes="99214"/>
        <procedure cptCodes="99215"/>
        <procedure snomedIds="12843005"/>
        <procedure snomedIds="18170008"/>
        <procedure snomedIds="185349003"/>
        <procedure snomedIds="185463005"/>
        <procedure snomedIds="185465003"/>
        <procedure snomedIds="19681004"/>
        <procedure snomedIds="207195004"/>
```
1310

```
  <or description="PHQ-9 assessment" period="reporting.period.index">
    <observation min="9" linkFilterName="Outpatient" loincTests="44249-1"/>
    <observation min="9" linkFilterName="Outpatient" loincTests="44257-4"/>
    <observation min="9" linkFilterName="Outpatient" loincTests="44261-6"/>
    <observation min="9" linkFilterName="Outpatient" loincTests="54635-8"/>
  </or>
```
1320

```xml
<linkFilters>
    <filter name="encounter">                                     — 1512
        <encounterLink linkType="ENCOUNTER">
            <or description="Outpatient encounter|Office visit|Observation|Osteopathic manipulative treatment">
                <encounter type="OFFICE_VISIT"/>
                <encounter type="OUTPATIENT"/>
                <procedure cptCodes="99397"/>
                <procedure cptCodes="99401"/>
                <procedure cptCodes="99402"/>
                <procedure cptCodes="99403"/>
                <procedure cptCodes="98925"/>
                <procedure cptCodes="98926"/>
                <procedure cptCodes="98927"/>
                <procedure cptCodes="98928"/>
                <procedure cptCodes="98929"/>
                <procedure cptCodes="98940"/>
                <procedure cptCodes="98941"/>
                <procedure cptCodes="98942"/>
            </or>                                                  — 1520

<temporalSequence uniqueResults="true">              — 1530
                <targetIndex>
                    <or description="ED encounter">
                        <encounter type="EMERGENCY"/>
                        <procedure cptCodes="99281"/>
                        <procedure cptCodes="99282"/>
                        <procedure cptCodes="99283"/>
                        <procedure cptCodes="99284"/>
                        <procedure cptCodes="99285"/>
                    </or>
                </targetIndex>
                <exclusionEvent negate="true" maxunits="MINUTES" max="1439" minunits="MINUTES" min="1">   ⎫
                    <criteria description="Inpatient encounter">                                          ⎬ 1540
                        <encounter type="INPATIENT"/>                                                     ⎭
                    </criteria>
                    <exclusion/>
                </exclusionEvent>
            </temporalSequence>
        </or>
    </encounterLink>
```

FIG.15

```
                    <not>                                1710
1715                  <or>
      <or description="Depression|Bipolar">
              <diagnosis linkFilterName="OutpatientOrOfficeVisitEncounter"
      icdCodes="F31.62"/>
              <diagnosis linkFilterName="OutpatientOrOfficeVisitEncounter"
      icdCodes="F31.63"/>
              <diagnosis linkFilterName="OutpatientOrOfficeVisitEncounter"
      icdCodes="F31.64"/>
              <diagnosis linkFilterName="OutpatientOrOfficeVisitEncounter"
      icdCodes="F31.75"/>
              <diagnosis linkFilterName="OutpatientOrOfficeVisitEncounter"
      icdCodes="F31.77"/>
              <diagnosis linkFilterName="OutpatientOrOfficeVisitEncounter"
      icdCodes="F31.81"/>
              <diagnosis linkFilterName="OutpatientOrOfficeVisitEncounter"
      icdCodes="F31.89"/>
1720          <diagnosis linkFilterName="OutpatientOrOfficeVisitEncounter"
      icdCodes="F33.41"/>
              <diagnosis linkFilterName="OutpatientOrOfficeVisitEncounter"
      icdCodes="F33.8"/>
              <diagnosis snomedIds="26862009"
      linkFilterName="OutpatientOrOfficeVisitEncounter"/>
              <diagnosis snomedIds="30605009"
      linkFilterName="OutpatientOrOfficeVisitEncounter"/>
              <diagnosis snomedIds="33135002"
      linkFilterName="OutpatientOrOfficeVisitEncounter"/>
              <diagnosis snomedIds="67002003"
      linkFilterName="OutpatientOrOfficeVisitEncounter"/>
              <diagnosis snomedIds="70747007"
      linkFilterName="OutpatientOrOfficeVisitEncounter"/>
              <diagnosis snomedIds="192099000"
      linkFilterName="OutpatientOrOfficeVisitEncounter"/>
      </or>
    </not>
```

FIG.17

```xml
-<not>
  -<or>
    -<or description="Depression|Bipolar">                                                   1910
        <diagnosis linkFilterName="OutpatientOrOfficeVisitEncounter" icdCodes="F31.62"/>
        <diagnosis linkFilterName="OutpatientOrOfficeVisitEncounter" icdCodes="F31.63"/>
        <diagnosis linkFilterName="OutpatientOrOfficeVisitEncounter" icdCodes="F31.64"/>
        <diagnosis linkFilterName="OutpatientOrOfficeVisitEncounter" icdCodes="F31.75"/>
        <diagnosis linkFilterName="OutpatientOrOfficeVisitEncounter" icdCodes="F31.77"/>
        <diagnosis linkFilterName="OutpatientOrOfficeVisitEncounter" icdCodes="F31.81"/>
        <diagnosis linkFilterName="OutpatientOrOfficeVisitEncounter" icdCodes="F31.89"/>
        <diagnosis linkFilterName="OutpatientOrOfficeVisitEncounter" icdCodes="F33.41"/>
        <diagnosis linkFilterName="OutpatientOrOfficeVisitEncounter" icdCodes="F33.8"/>
        <diagnosis snomedIds="26862009"
linkFilterName="OutpatientOrOfficeVisitEncounter"/>
        <diagnosis snomedIds="30605009"
linkFilterName="OutpatientOrOfficeVisitEncounter"/>
        <diagnosis snomedIds="33135002"
linkFilterName="OutpatientOrOfficeVisitEncounter"/>
        <diagnosis snomedIds="67002003"
linkFilterName="OutpatientOrOfficeVisitEncounter"/>
        <diagnosis snomedIds="70747007"
linkFilterName="OutpatientOrOfficeVisitEncounter"/>
        <diagnosis snomedIds="192099000"
linkFilterName="OutpatientOrOfficeVisitEncounter"/>
    </or>
    -<or description="Depression screening">                                                 1920
        <procedure cptCodes="S3005" snomedIds=""
linkFilterName="OutpatientOrOfficeVisitEncounter"/>
        <diagnosis snomedIds="" linkFilterName="OutpatientOrOfficeVisitEncounter"
icdCodes="V79.0"/>
        <diagnosis linkFilterName="OutpatientOrOfficeVisitEncounter" icdCodes="Z13.89"/>
        <procedure snomedIds="171207006"
linkFilterName="OutpatientOrOfficeVisitEncounter"/>
    </or>
  </or>
</not>
```

1905 points to the overall structure.

Numerator Reference Tables 2360

| N1 | | |
|---|---|---|
| | ✔ Tobacco use | |
| | Diagnosis | |
| | SNOMED | 160603005, 160604004, 160605003, 160606002, 160618003, 160644005, 228454005, 228504007, 228514003, 228515002, 228516001, 228517005, 228519000, 230058006, 230059003, 230060008, 230063004, 266918002, 266920004, 401199007, 428041000124106, 428061000124103, 428971000124105, 449868002, 56977008, 65568007, 77176002, 81703003, 82302208 |
| | Procedures | |
| | CPT | 1034F, 1035F |
| | Tobacco | |
| | Cessation Codes | |
| | Tobacco User: YES | |

| N2 | | |
|---|---|---|
| | ✔ Smoking cessation agent ✔ Smoking cessation counseling | |
| | Drug | |
| | Rxnorm | 1046647, 1046653, 1150773, 151226, 198029, 198030, 198031, 198045, 198046, 198047, 198405, 198407, 1996077, 199888, 199889, 199890, 205315, 205316, 250983, 252413, 311672, 311975, 312036, 314119, 317136, 359817, 359816, 359827, 359835, 359836, 359857, 359875, 359881, 749785, 852244, 896163, 898335, 898366, 898338, 898541, 898553, 898557, 898637, 898671, 898676, 898679 |
| | Procedures | |
| | CPT | 4004F, 99406, 99407 |

FIG. 23C

Reference Periods

START
12:00:01 AM
MM/DD/YYYY

→ STOP
12:00:00 AM
MM/DD/YYYY

Different criteria in each measure require that records occur during a precise time period. Note that all dates begin at midnight.

Operators

Operators describe what criteria is needed for a measure. They include:

— AND
Both criteria above and below the line must be met

— OR
Either criteria above or below the line must be met

[NONE OF THE FOLLOWING]
The criteria following this are negated — they must not have occurred

Expressions

You will encounter certain expressions that denote a specific relationship between criteria. They include:

● Linked Encounter
Indicates that the criteria listed above must have occurred during the same encounter as the criteria that immediately follows ◐ HAPPENS AFTER
Indicates that the criteria must have occurred in a certain sequence. The criteria that follows must have occurred after the criteria listed above ◐ HAPPENED PREVIOUSLY
Reverse sequence — the criteria that follows must have occurred before the criteria listed above ⊕ COUNT INSTANCES
The first criteria specifies what must be on the patient record. The criteria below is then counted for that patient

VALIDATING AND VISUALIZING PERFORMANCE OF ANALYTICS

BACKGROUND

1. Technical Field

Present invention embodiments relate to performing analytics on data stored within data systems, and more specifically, to validating and visualizing performance of the analytics to ensure proper operation.

2. Discussion of the Related Art

Healthcare networks have very complicated organization structures. An organization typically comprises multiple source systems (e.g., a source of electronic medical records including electronic health records (EHR), records from a claims system, lab feed, various data sources implementing the HL7 standard, patient satisfaction survey, etc.). Clinically integrated networks (CIN) or galaxies (e.g., a group of organizations) are collections of individual healthcare systems with data sharing agreements. Analytics may be applied to the various electronic medical records to produce results for a desired population (e.g., of patients, health care providers, provider organizations or networks, etc.) based upon queries by end users.

The analytics determine measures for particular patient populations, where the measures are defined by specifications within a schema used to analyze the data (e.g., an XML type language). Patients are assigned to categories based on satisfaction of criteria for a measure, and values of organization performance for a measure are determined based on the number of patients in each category. These performance values are utilized to understand the performance of the organization which affects reimbursement or overall cost savings.

When new measures are to be employed, the new measures are validated, typically as user acceptance testing, to ensure that the new measures are working properly and capturing any requested customization. However, this validation process is performed manually, where users receive and manually analyze combinations of specification documents to understand how those measures work and the corresponding criteria. Subsequently, users manually view patient information to identify evidence (or lack of evidence) to apply to measure criteria in order to ensure that the measure is properly sorting patients.

The manual validation process is inefficient due to a lack of understanding by users of the measure criteria which facilitates loss of measure specifics (such as date ranges that apply to certain diagnoses and procedures) and lack of confidence in results. In addition, the process is extremely time intensive since users need to manually search through patient information.

SUMMARY

According to one embodiment of the present invention, a system detects conditions for analytics and includes at least one processor. The system analyzes a structured document including a plurality of sections each specifying a set of conditions for members of a population in a structured format. The structured document is utilized to perform an analytic on the population. Each section within the structured document is identified and a corresponding set of conditions for that identified section in the structured format is extracted. The corresponding extracted set of conditions for each section is translated to an unstructured format for visual presentation of each identified section with a description of the corresponding set of conditions. Embodiments of the present invention further include a method and computer program product for detecting conditions for analytics in substantially the same manner described above.

BRIEF DESCRIPTION OF THE DRAWINGS

Generally, like reference numerals in the various figures are utilized to designate like components.

FIG. 7 illustrates example portions of a measure specification in a structured document providing descriptions of measure components according to an embodiment of the present invention.

FIG. 9 illustrates example portions of a measure specification in a structured document providing grouped measure components according to an embodiment of the present invention.

FIG. 11 illustrates example portions of a measure specification in a structured document providing a temporal sequence of conditions according to an embodiment of the present invention.

FIG. 13 illustrates example portions of a measure specification in a structured document linking conditions according to an embodiment of the present invention.

FIG. 15 illustrates example portions of a measure specification in a structured document providing complex linking of conditions according to an embodiment of the present invention.

FIG. 17 illustrates example portions of a measure specification in a structured document providing conditions that are required to not occur for the measure according to an embodiment of the present invention.

FIG. 19 illustrates example portions of a measure specification in a structured document providing a complex arrangement of conditions that are required to not occur for the measure according to an embodiment of the present invention.

FIGS. 23A-23D are example schematic illustrations of visualizations produced from a measure specification according to an embodiment of the present invention.

DETAILED DESCRIPTION

Figure 1:
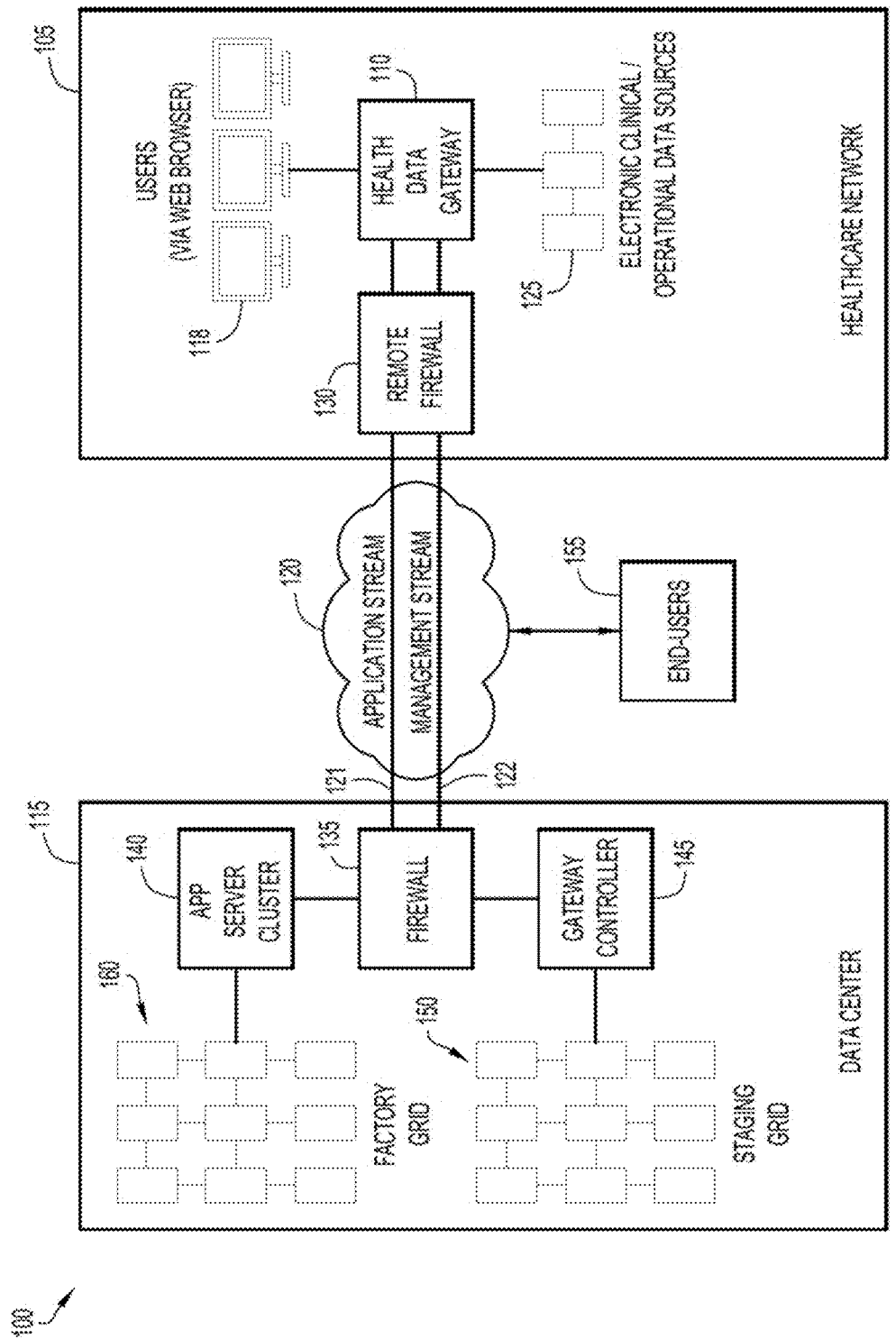
FIG. 1 is a diagrammatic illustration of an example computing environment according to an embodiment of the present invention.

An organization may comprise multiple source systems (e.g., a source of electronic medical records including electronic health records (EHR), records from a claims system, lab feed, various data sources implementing the HL7 standard, patient satisfaction survey, etc.), while clinically integrated networks (CIN) or galaxies (e.g., a group of organizations) are collections of individual healthcare systems with data sharing agreements.

Analytics may be applied to the various electronic medical records to produce results for a desired population (e.g., of patients, health care providers, provider organizations or networks, etc.) based upon queries by end users. The analytics determine one or more measures for a desired patient population. A measure is specified within a structured document by a specification employing an Extensible Markup (XML) type language or other language indicating the criteria or definition for the measure. The measure typically includes a numerator and a denominator. For example, a measure may produce a value for diabetic patients having a body mass index (BMI) within a certain range. The denominator represents the quantity (or population) of patients diagnosed with diabetes, while the numerator represents the quantity of patients diagnosed with diabetes and having a BMI within the specified range. However, a measure may include any desired quantity and combinations of conditions for the numerator and denominator.

The specification for a measure includes sections for the numerator and denominator delineated by tags or other identifiers with each section specifying the criteria or conditions for patients to be included within the respective numerator and denominator. Present invention embodiments analyze the measure specification to validate and provide detailed output about the measure comprehendible by a user in various manners.

For example, present invention embodiments may visualize and provide details pertaining to a measure previously unknown to a user in order to reduce confusion. Present invention embodiments isolate each core element of a measure and represent those core elements as something resembling steps or actions, thereby reducing omissions of primary portions of the measure. Further, the primary aspects of the measure are emphasized, where the need to constantly cross-reference measure portions and data is reduced.

Complicated and compound aspects of a measure are simplified and decomposed. For example, an analysis may provide indications for a measure that: an encounter or event may be linked to a medical diagnosis; an exact time range affects a certain portion of the measure; or a time elapsed between one event and occurrence of a second event. A document (e.g., PDF or other document format) containing visualizations is generated directly from the language defining the measure within the measure specification. This removes the role of individuals maintaining documents and minimizes the risk of human error. In addition, an accurate reference date may be determined for the measure based on the analysis to calculate time ranges specific to viewing of the measure.

Moreover, the automated output may be provided within a context of specific patients. For example, present invention embodiments may specify measure characteristics for a patient (e.g., an exact sequence of measure criteria, number of measure criteria, etc.), and corresponding evidence showing compliance by the patient. The output may further capture requested customizations (e.g., from a steward specification).

An example computing environment for use with present invention embodiments is illustrated in FIG. 1. Computing environment 100 includes a healthcare network 105 in communication with a data center 115 over a communications network 120 (e.g., providing a secure virtual private network (VPN)). The communications over network 120 preferably occur between a firewall 130 of healthcare network 105 and a firewall 135 of data center 115. The communications over network 120 may include an application stream 121 pertaining to communications for applications and a management stream 122 pertaining to communications for managing the data. The network may be implemented by any number of any suitable communications media (e.g., wide area network (WAN), local area network (LAN), Internet, Intranet, etc.). Alternatively, healthcare network 105 and data center 115 may be local to each other, and communicate via any appropriate local communication medium (e.g., local area network (LAN), hardwire, wireless link, Intranet, etc.).

Healthcare network 105 includes a health data gateway 110 coupled to end-user systems 118 and one or more clinical/operational data sources 125 providing various medical information (e.g., electronic health records (EHR), records from a claims system, lab feed, various data sources implementing the HL7 standard, patient satisfaction survey, etc.) stored according to a source data model.

Data center 115 includes an application server cluster 140, a gateway controller 145, a staging grid 150, and a factory grid 160. Health data gateway 110 of healthcare network 105 is configured to acquire data from data sources 125 and transmit the acquired data to gateway controller 145 of data center 115. The gateway controller receives the incoming data from the communications network and processes that data to staging grid 150. The staging and factory grids each include a cluster of computer systems to store data and perform parallel processing. By way of example, the staging and factory grids each employ a HADOOP cluster with a HADOOP distributed file system (HDFS).

Staging grid 150 inspects and publishes the data to factory grid 160 in accordance with a data model employed by the factory grid. Factory grid 160 includes various engines to perform desired analytics on the data based on queries received from end-user systems 118 and other end-user systems 155 accessing data center 115 over network 120. The queries are handled in conjunction with application server cluster 140 to produce desired results.

Figure 2:
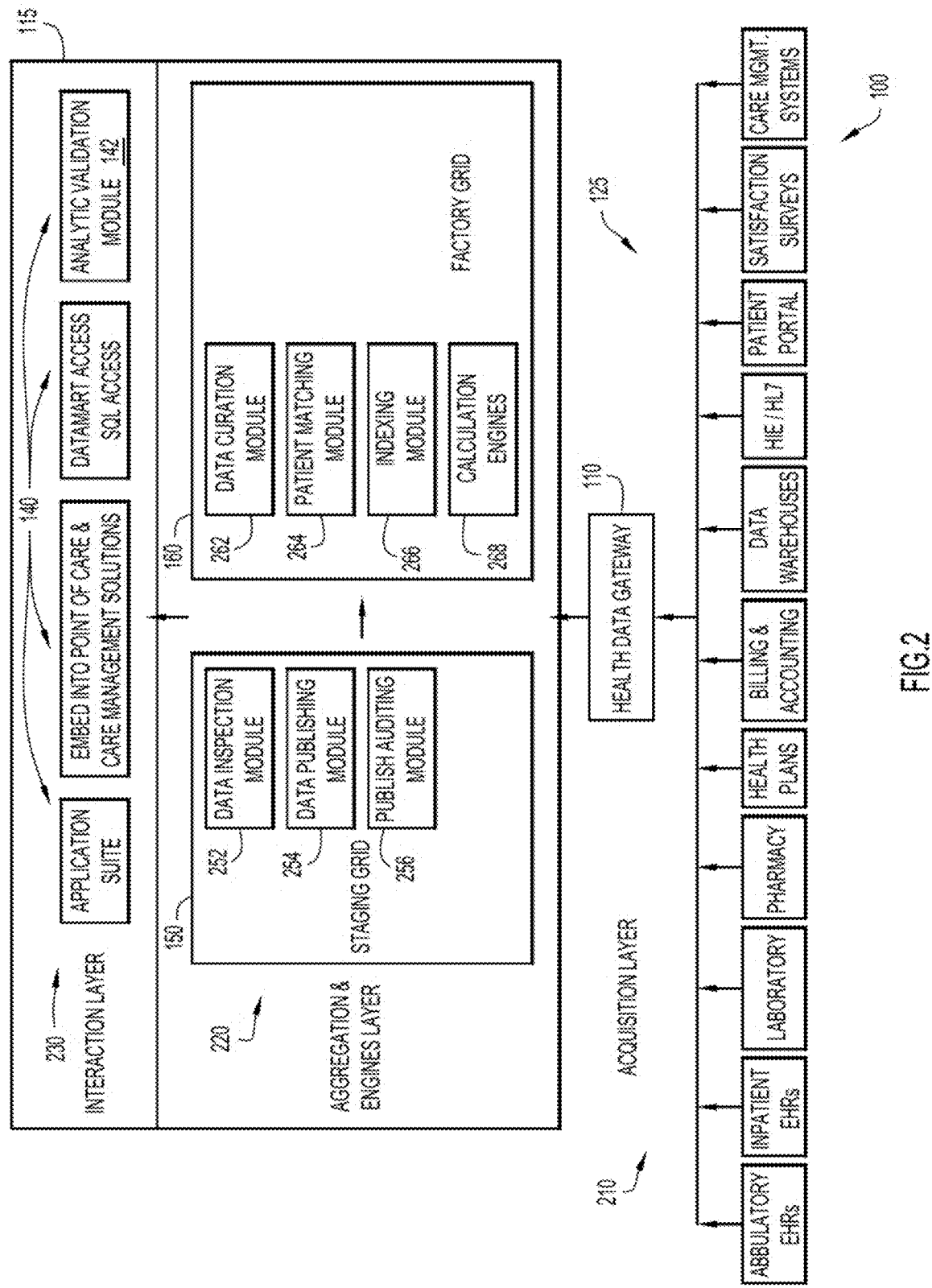
FIG. 2 is a diagrammatic illustration of the data center of the computing environment of FIG. 1 according to an embodiment of the present invention.

Referring to FIG. 2, health data gateway 110 of one or more healthcare networks is configured to acquire data from data sources 125 of those healthcare networks (e.g., ambulatory electronic health records (EHR), inpatient electronic health records (EHR), laboratory data, pharmacy data, health plan data, billing and accounting data, data warehouses, health information exchange (HIE)/HL7 data, patient portal, satisfaction surveys, care management systems, etc.) and transmit the acquired data to gateway controller 145 of data center 115 as described above. The healthcare networks and/or data sources 125 form an acquisition layer 210 providing data to data center 115 via health data gateway 110.

Gateway controller 145 receives the incoming data from communications network 120 and processes that data to staging grid 150 employing data models of the source systems. Staging grid 150 includes a data inspection module 252, a data publishing module 254, and a publish auditing module 256 to inspect, publish, and audit the data to factory grid 160 in accordance with the data model employed by the factory grid.

Factory grid 160 includes a data curation module 262, a patient matching module 264, an indexing module 266, and various calculation/analytic engines 268. Data curation module 262 performs data curation operations including mapping codes, data cleansing, and standardization, while patient matching module 264 performs patient matching operations to determine records associated with the same patient. Indexing module 266 performs indexing operations including combining records based on patient matching, mappings, and application of risk models. The calculation/analytic engines execute measure specifications, and perform the desired analytics based on queries received from end-users from an interaction layer 230 enabling application server cluster 140 to provide various applications for processing and accessing the data (e.g., analytic applications, SQL access, etc.). Application server cluster 140 includes an analytic validation module 142 to analyze a measure specification and validate the measure as described below. The staging and factory grids form an aggregation and engines layer 220 to process the acquired data, while the queries are handled by factory grid 160 in conjunction with application server cluster 140 to produce desired results for the interaction layer.

The various applications of application server cluster 140 may be provided in a cloud environment. It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones or other devices, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly release to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

Figure 3:
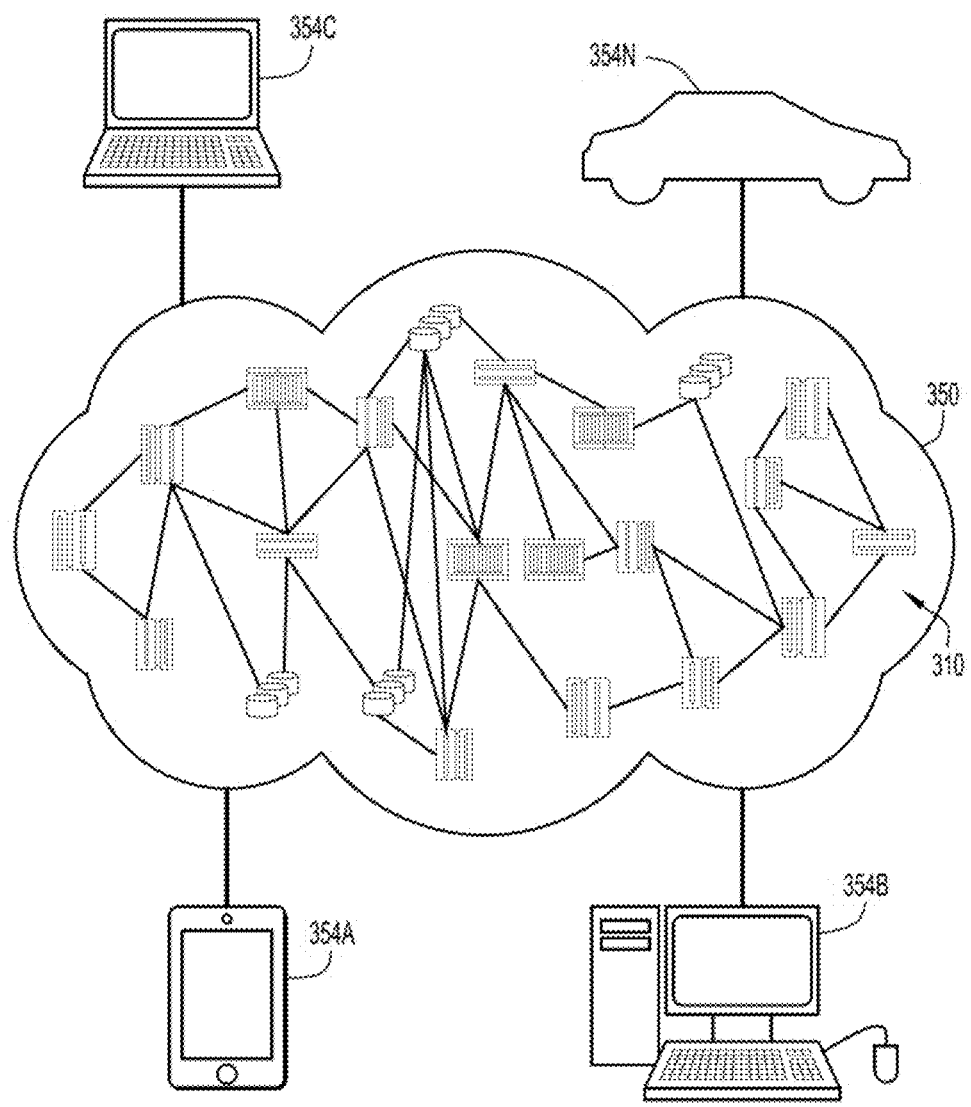
FIG. 3 is a diagrammatic illustration of an example cloud computing environment for the computing environment of FIG. 1 according to an embodiment of the present invention.

A cloud computing environment is service oriented with a focus on statelessness, low coupling, modularity, and semantic interoperability. At the heart of cloud computing is an infrastructure comprising a network of interconnected nodes. Referring now to FIG. 3, illustrative cloud computing environment 350 is depicted. As shown, cloud computing environment 350 comprises one or more cloud computing nodes 310 with which local computing devices used by cloud consumers, such as, for example, personal digital assistant (PDA) or cellular telephone 354A, desktop computer 354B, laptop computer 354C, and/or automobile computer system 354N may communicate. Nodes 310 may communicate with one another. They may be grouped (not shown) physically or virtually, in one or more networks, such as Private, Community, Public, or Hybrid clouds as described hereinabove, or a combination thereof. This allows cloud computing environment 350 to offer infrastructure, platforms and/or software as services for which a cloud consumer does not need to maintain resources on a local computing device. It is understood that the types of computing devices 354A-N shown in FIG. 3 are intended to be illustrative only and that computing nodes 310 and cloud computing environment 350 can communicate with any type of computerized device over any type of network and/or network addressable connection (e.g., using a web browser).

Figure 4:
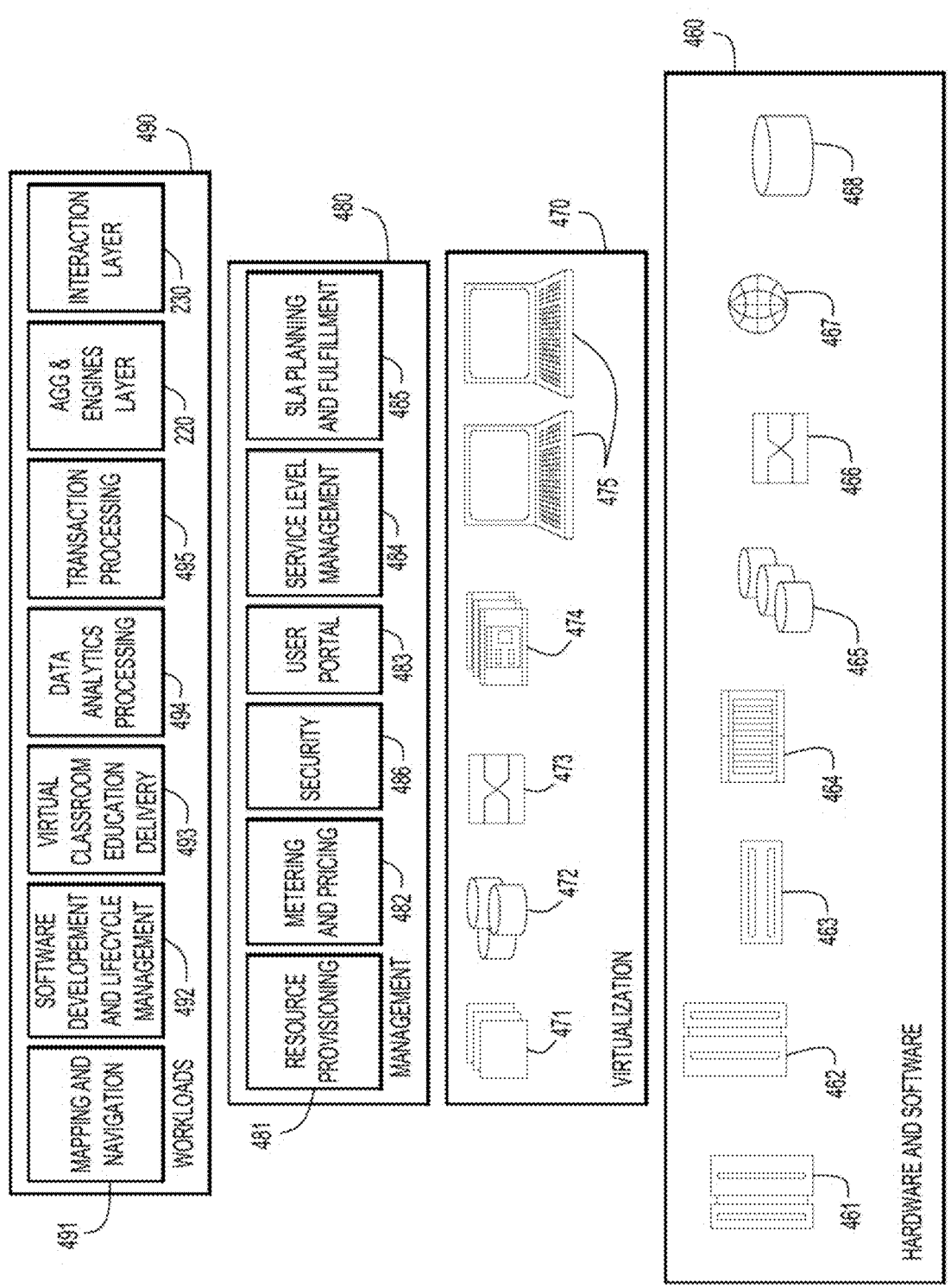
FIG. 4 is a diagrammatic illustration of abstraction model layers according to an embodiment of the present invention.

Referring now to FIG. 4, a set of functional abstraction layers provided by cloud computing environment 350 (FIG. 3) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 460 includes hardware and software components. Examples of hardware components include: mainframes 461; RISC (Reduced Instruction Set Computer) architecture based servers 462; servers 463; blade servers 464; storage devices 465; and networks and networking components 466. In some embodiments, software components include network application server software 467 and database software 468.

Virtualization layer 470 provides an abstraction layer from which the following examples of virtual entities may be provided: virtual servers 471; virtual storage 472; virtual networks 473, including virtual private networks; virtual applications and operating systems 474; and virtual clients 475.

In one example embodiment, management layer 480 may provide some or all of the functions for data center 115 described herein. Resource provisioning 481 provides dynamic procurement of computing resources and other resources that are utilized to perform tasks within the cloud computing environment. Metering and Pricing 482 provide cost tracking as resources are utilized within the cloud computing environment, and billing or invoicing for consumption of these resources. In one example, these resources may comprise application software licenses. Security 486 provides identity verification for cloud consumers and tasks, as well as protection for data and other resources. User portal 483 provides access to the cloud computing environment for consumers and system administrators. Service level management 484 provides cloud computing resource allocation and management such that required service levels are met. Service Level Agreement (SLA) planning and fulfillment 485 provide pre-arrangement for, and procurement of, cloud computing resources for which a future requirement is anticipated in accordance with an SLA.

Workloads layer 490 provides examples of functionality for which the cloud computing environment may be utilized. Examples of workloads and functions which may be provided from this layer include: mapping and navigation 491; software development and lifecycle management 492; virtual classroom education delivery 493; data analytics processing 494; transaction processing 495; aggregation and engines layer 220 (FIG. 2); and interaction layer 230 (FIG. 2).

Figure 5:
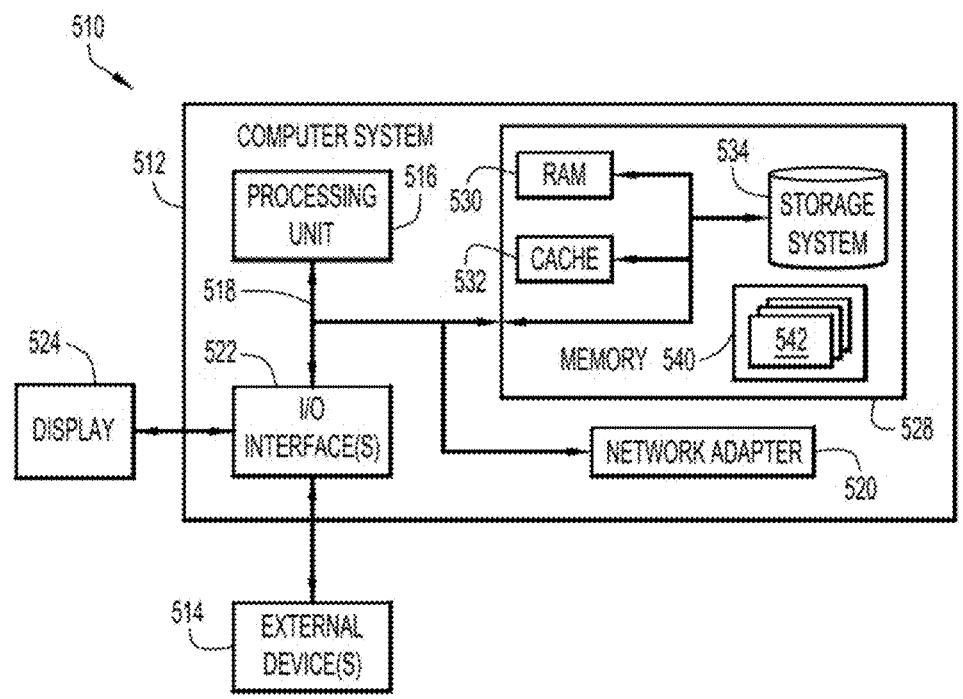
FIG. 5 is a block diagram of a computing node according to an embodiment of the present invention.

Referring now to FIG. 5, a schematic of an example of a computing node or device 510 of computer environment 100 (e.g., health data gateway 110, application server cluster 140, gateway controller 145, computing nodes of staging grid 150, computing nodes of factory grids 160, etc.) and cloud environment 350 (e.g., cloud computing node 310, etc.) is shown. The computing node or device is only one example of a suitable computing node for computing environment 100 and cloud computing environment 350 and is not intended to suggest any limitation as to the scope of use or functionality of embodiments of the invention described herein. Regardless, computing node 510 is capable of being implemented and/or performing any of the functionality set forth herein.

In computing node 510, there is a computer system 512 which is operational with numerous other general purpose or special purpose computing system environments or configurations. Examples of well-known computing systems, environments, and/or configurations that may be suitable for use with computer system 512 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 512 may be described in the general context of computer system executable instructions, such as program modules, being executed by a computer system. Generally, program modules may include routines, programs, objects, components, logic, data structures, and so on that perform particular tasks or implement particular abstract data types. Computer system 512 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system 512 is shown in the form of a general-purpose computing device. The components of computer system 512 may include, but are not limited to, one or more processors or processing units 516, a system memory 528, and a bus 518 that couples various system components including system memory 528 to processor 516.

Bus 518 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 512 typically includes a variety of computer system readable media. Such media may be any available media that is accessible by computer system 512, and it includes both volatile and non-volatile media, removable and non-removable media.

System memory 528 can include computer system readable media in the form of volatile memory, such as random access memory (RAM) 530 and/or cache memory 532. Computer system 512 may further include other removable/non-removable, volatile/non-volatile computer system storage media. By way of example only, storage system 534 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 518 by one or more data media interfaces. As will be further depicted and described below, memory 528 may include at least one program product having a set (e.g., at least one) of program modules that are configured to carry out the functions of embodiments of the invention.

Program/utility 540, having a set (at least one) of program modules 542, may be stored in memory 528 by way of example, and not limitation, as well as an operating system, one or more application programs, other program modules, and program data. Each of the operating system, one or more application programs, other program modules, and program data or some combination thereof, may include an implementation of a networking environment. Program modules 542 generally carry out the functions and/or methodologies of embodiments of the invention as described herein.

Computer system 512 may also communicate with one or more external devices 514 such as a keyboard, a pointing device, a display 524, etc.; one or more devices that enable a user to interact with computer system 512; and/or any devices (e.g., network card, modem, etc.) that enable computer system 512 to communicate with one or more other computing devices. Such communication can occur via Input/Output (I/O) interfaces 522. Still yet, computer system 512 can communicate with one or more networks such as a local area network (LAN), a general wide area network (WAN), and/or a public network (e.g., the Internet) via network adapter 520. As depicted, network adapter 520 communicates with the other components of computer system 512 via bus 518. It should be understood that although not shown, other hardware and/or software components could be used in conjunction with computer system 512. Examples, include, but are not limited to: microcode, device drivers, redundant processing units, external disk drive arrays, RAID systems, tape drives, and data archival storage systems, etc.

Figure 6A:
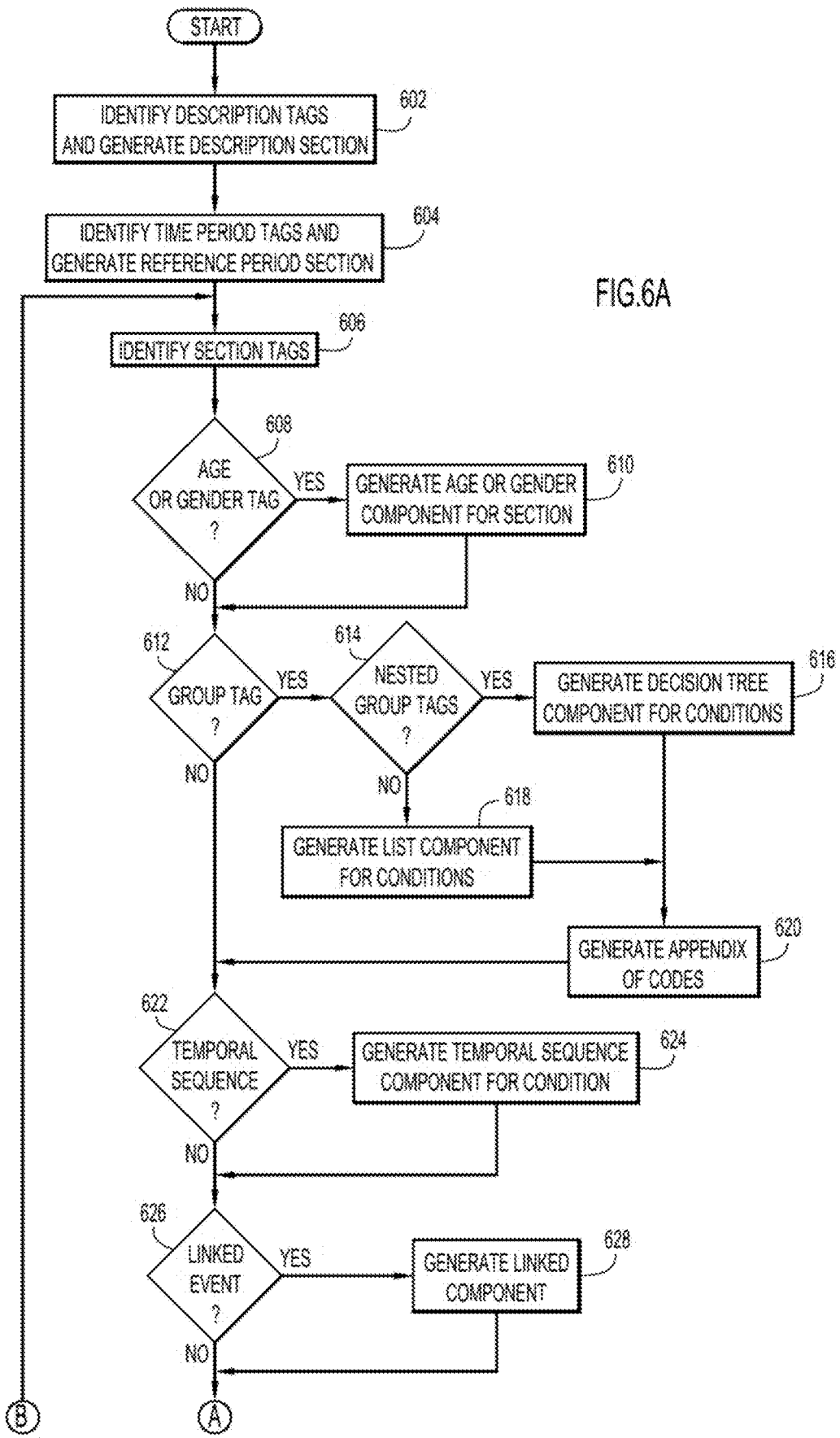
FIGS. 6A-6B are a procedural flowchart illustrating a manner of analyzing a measure specification according to an embodiment of the present invention.
Figure 6B:
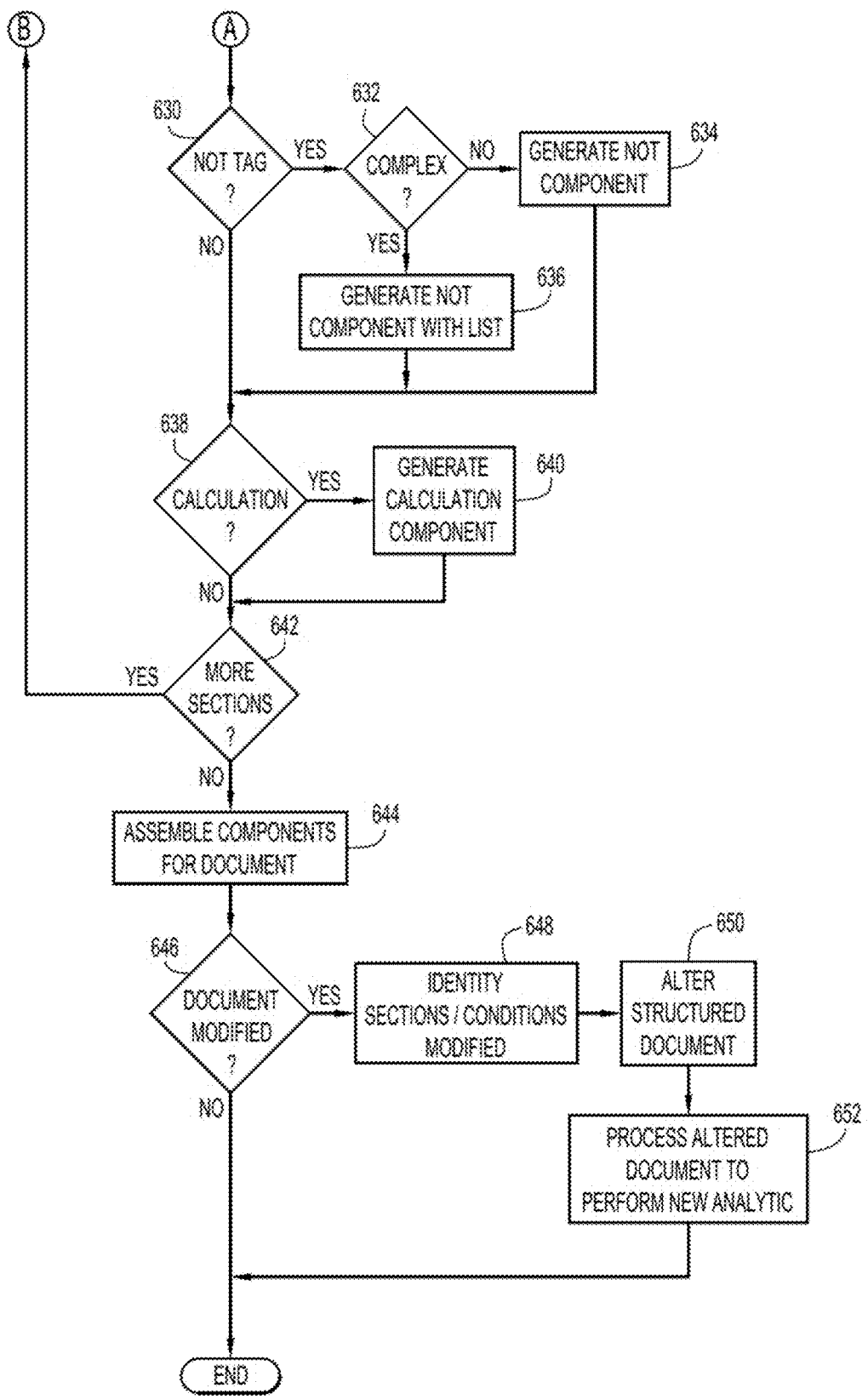

A manner of analyzing a measure specification (e.g., via analytic validation module 142 and application server cluster 140) to visualize and validate the measure is illustrated in FIGS. 6A-6B. Initially, analytics or measures may be utilized to render various determinations (e.g., to determine one or more measures for a desired patient population and/or registry of health care providers, to determine an attribution to attribute a patient to a healthcare provider, etc.). An analytic or measure is specified within a specification document by a specification employing an XML type language indicating the criteria or definition for the measure. The measure typically includes a numerator and a denominator. The specification for a measure includes various sections delineated by tags or other identifiers, where the sections specify information and/or the criteria or conditions associated with that section (e.g., numerator, denominator, exclusions, exceptions, etc.).

The measure specification within a specification document is analyzed to identify description tags or other identifiers indicating description information at step 602. The description information is extracted from the specification document to generate a description section 800 (FIG. 8) for an output document containing visualizations for the specification document. For example, the measure specification (FIG. 7) may include: a measure description section 710 (e.g., delineated by a description tag), an improvement section 720 (e.g., delineated by a target tag), and analytic component section 740 (e.g., with each component delineated by a corresponding tag (e.g., for a denominator, numerator, exclusion, and exception)).

Each section corresponds to a portion of description section 800 (FIG. 8) of the output document, where description information from a section of the measure specification is extracted and placed in a corresponding visualization section of the output document. The tags of the measure specification provide a mapping between the measure specification and output document for placement of the description information. When there is no tag in the measure specification for a corresponding visualization section of the output document (e.g., an exclusion tag), the corresponding visualization section of the output document may indicate "None." When the tag does exist in the measure specification without a description, the corresponding visualization section of the output document may be blank (e.g., exclusion section 846 of FIG. 8).

Figure 8:
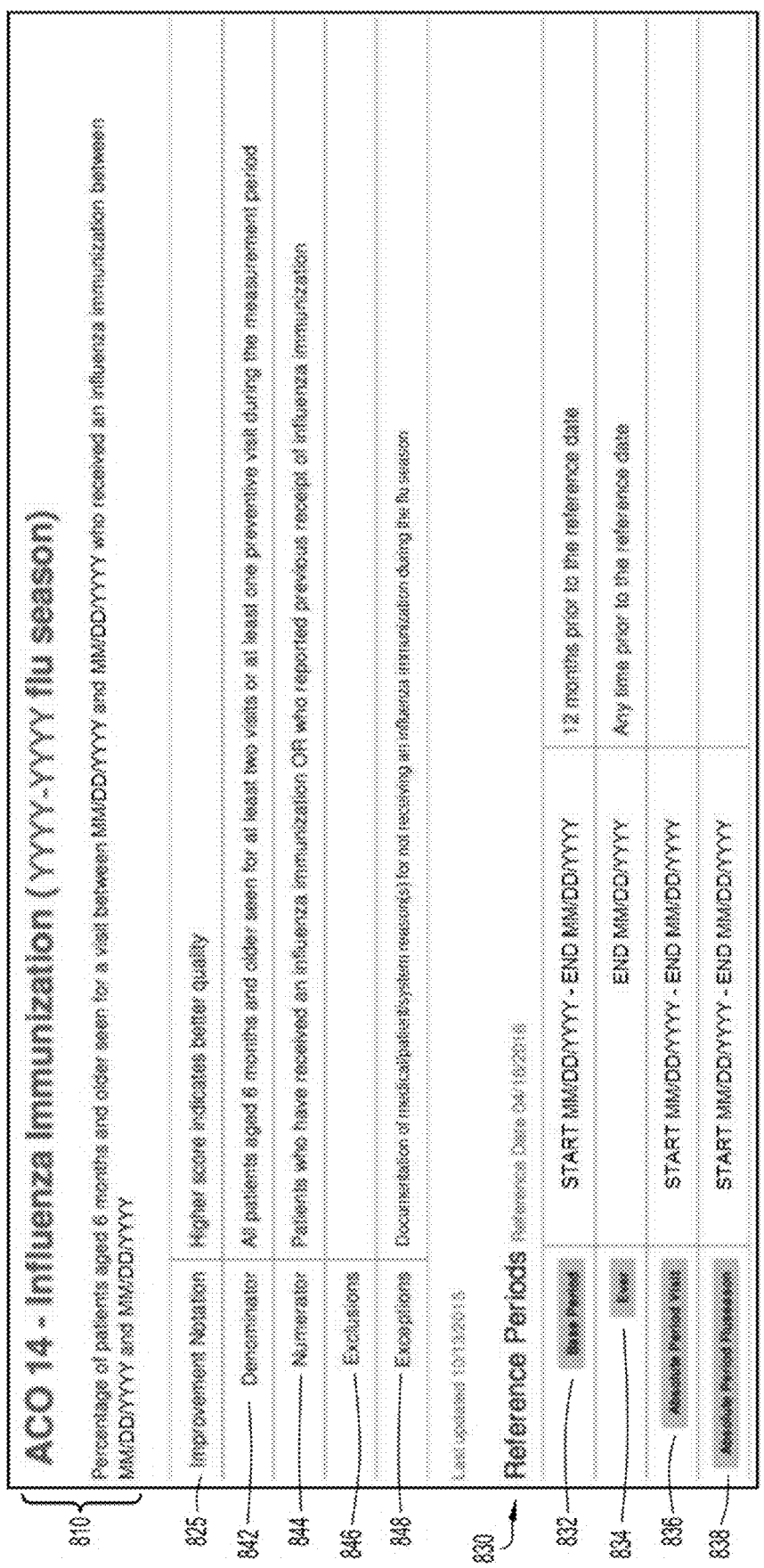
FIG. 8 is a schematic illustration of a visualization from the example portions of the measure specification illustrated in FIG. 7 according to an embodiment of the present invention.

For example, measure description section 710 of the measure specification (e.g., delineated by a description tag) contains a description of the measure. This information is extracted and placed in a corresponding visualization section 810 of the output document (FIG. 8). The name of the measure in the output document is derived from a title listed in an application (and not from the measure specification).

Improvement section 720 of the measure specification (e.g., delineated by a target tag) contains an improvement indicator 725. This information is extracted and placed in a corresponding visualization section 825 of the output document (FIG. 8). By way of example, when indicator 725 indicates ABOVEOREQUAL, the output document may be generated to indicate "Higher score indicates better quality" in visualization section 825 (e.g., as viewed in FIG. 8).

However, when indicator 725 indicates BELOWOREQUAL, the output document may be generated to indicate "Lower score indicates better quality" in visualization section 825.

Analytic component section 740 of the measure specification (e.g., with each component delineated by a corresponding tag (e.g., for a denominator, numerator, exclusion, and exception)) contains various description components, including a denominator description component 742, a numerator description component 744, an exclusion description component 746, and an exception description component 748. Denominator description component 742 contains a description of the denominator for the measure. This information is extracted and placed in a corresponding visualization section 842 of the output document (FIG. 8). Numerator description component 744 contains a description of the numerator for the measure. This information is extracted and placed in a corresponding visualization section 844 of the output document (FIG. 8). Exclusion description component 746 contains a description of exclusions (e.g., conditions for excluding patients from the measure component). This information is extracted and placed in a corresponding visualization section 846 of the output document (e.g., a blank as shown in FIG. 8). Exception description component 748 contains a description of exceptions (e.g., criteria to be excepted from the numerator and not included in the measure calculation; however, these excepted patients meet the denominator criteria). This information is extracted and placed in a corresponding visualization section 848 of the output document (FIG. 8).

Once the above visualization sections have been generated for the output document, the measure specification within the specification document is further analyzed to identify reference time period tags or other identifiers indicating reference time periods at step 604 (FIG. 6A). The measure specification (FIG. 7) may include a reference time period section 730 (e.g., with each time period delineated by a corresponding tag (e.g., base period, ever period, and absolute period)).

Reference time period section 730 of the measure specification (e.g., with each time period delineated by a corresponding tag (e.g., base period, ever period, and absolute period)) contains various time period components, including a base period component 732, an ever period component 734, and absolute period components 736, 738. These specify periods of time and are parsed into a name and, if applicable, a time range and description for visualization section 830 (FIG. 8) of the output document. For example: a base period tag corresponds to a name "Base Period" in corresponding visualization section 832 of the output document, while an ever period tag corresponds to a name "Ever" in corresponding visualization section 834 of the output document. An absolute period or reference period tag corresponds to a name of the identification in the tag in corresponding visualization sections 836 and 838 of the output document (e.g., absolute.period.visit becomes "Absolute Period Visit" in visualization section 836 of the output document as viewed in FIG. 8).

Base period component 732 indicates a duration in the specified units (e.g., months as viewed in FIG. 7) relative to a specified reference date. This information is converted to start and end dates for the time period and placed in corresponding visualization section 832 of the output document. A description for visualization section 832 of the output document may be of the form "[duration] [duration unit] [prior to/after] the reference date" (e.g., "12 months prior to the reference date" as viewed in FIG. 8). The value (e.g., negative or positive) of the duration determines the language of the description (e.g., prior or after the reference date).

Ever period time range component 734 indicates a reference date, and is converted to a time period with a blank start date and ending with the reference date in corresponding visualization section 834 of the output document. The corresponding visualization section of the output document may further indicate that the time period is anytime before the ending or reference date (e.g., "Any time prior to the reference date" as viewed in FIG. 8).

A reference period component (not shown) may include a time range with a starting value determined by a start offset and unit, and an ending value indicated by an end offset and unit. The offset is based on a reference time period. For example, when a reference date is 11/1/YYYY, the reference time period is the base period of 12 months, the start offset is −2 YEARS, and the end offset is −1 YEARS, the resulting date range is 11/1/(YYYY −3) to 11/1/(YYYY −1) which is provided in the corresponding visualization section of the output document.

A description for the reference period in the output document depends on the offset. When the start and end offset are both −1 YEARS, the description may be of the form "1 year prior to [reference time period]". When there is no start offset, and the end offset is −364 DAYS, the description may be of the form "The first day of the measurement year." When there is a value for the start but not for the end, the description may be of the form "[start offset] [start unit] [prior to/after] start date of [reference time period]". If there is a start offset and no end offset, the description may be of the form "[start offset] [start unit] [prior to/after] start date of [reference time period]". If there is an end offset and no start offset, the description may be of the form "[end offset] [end unit]".

Absolute period components 736, 738 indicate a time range determined by a start year, start month, start day, end year, end month, and end day. These parameters are used to determine a date range which is placed in corresponding visualization sections 836, 838 of the output document (FIG. 8). These corresponding sections are generally not provided with a description.

The measure specification may contain various component sections to define different components for a measure, each delineated by tags or other identifiers (e.g., numerator, denominator, exclusions, exceptions, etc.). A component section (for a measure component) is identified at step 606 (FIG. 6A) based on tags within the measure specification, and a corresponding visualization section is generated in the output document. For example, a component section may include start and end tags within the measure specification to delineate that section (or measure component). By way of example, denominator tags 910 (FIG. 9) within a measure specification may be utilized to specify a component section for a denominator component of that measure, where a corresponding denominator visualization section 1050 (FIG. 10) may be generated in the output document.

Figure 10:
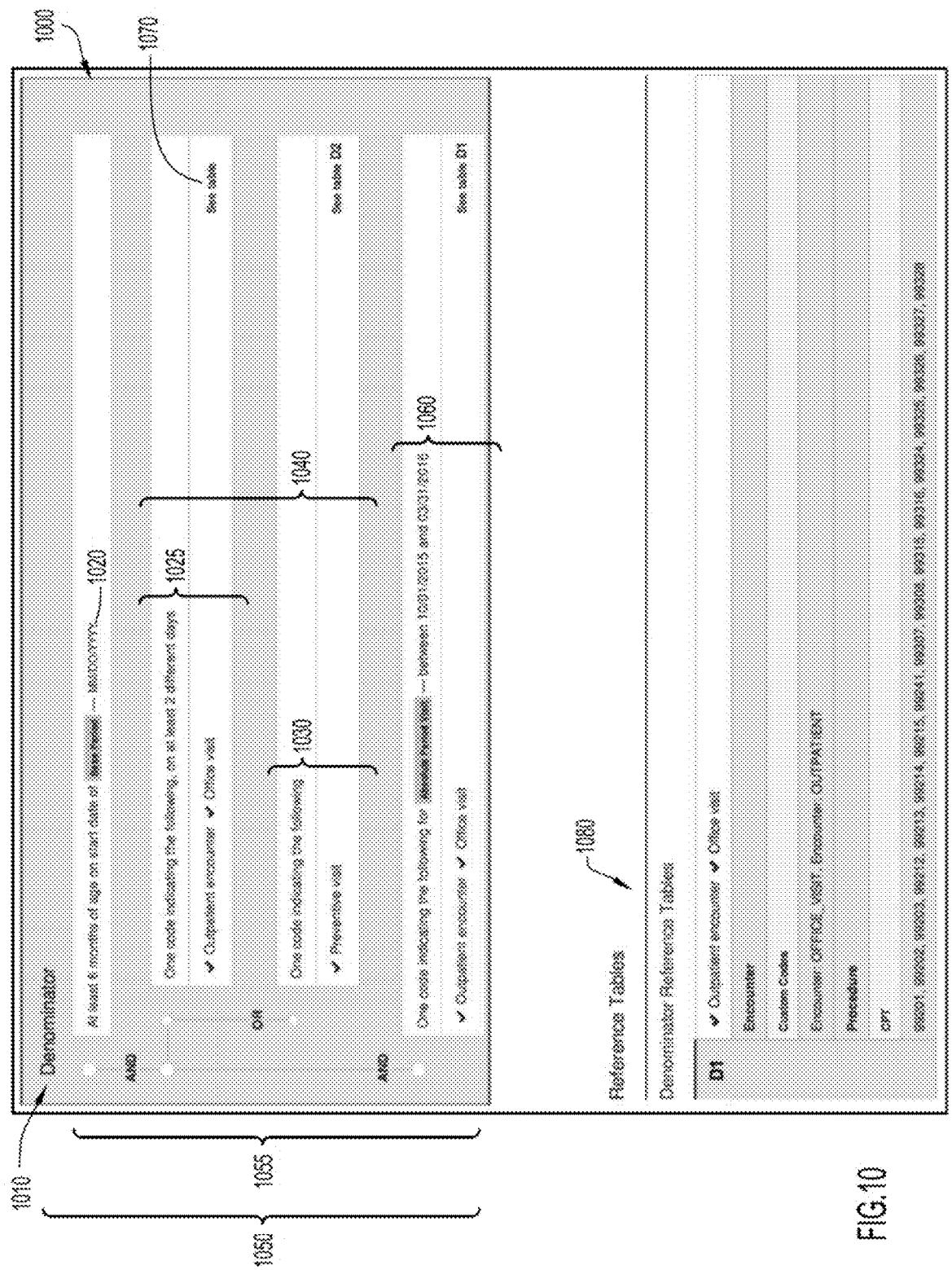
FIG. 10 is a schematic illustration of a visualization from the example portions of the measure specification illustrated in FIG. 9 according to an embodiment of the present invention.

Further, various types of tags (e.g., age, gender, logic, group, temporal sequence, linked events, not, calculation, etc.) may reside within the delineated section to provide different aspects for the measure component. The information corresponding to the tags are extracted and/or processed to generate a corresponding visualization section for an output document (FIG. 10). For example, the measure specification (FIG. 9) may include: a denominator section 950 (e.g., delineated by denominator tags), an age section 920 (e.g., delineated by an age tag), a group type section 925

(e.g., delineated by a group tag), and logical OR constructs 930, 940, 960 (delineated by an OR tag).

Each component and aspect section corresponds to a portion 1000 of the output document (FIG. 10), where information from a component or aspect section of the measure specification is extracted and/or processed and placed in a corresponding visualization section of the output document. The tags of the measure specification provide a mapping between the measure specification and output document for placement of the information.

When an age or gender tag is encountered within the identified component section as determined at step 608 (FIG. 6A), a corresponding age or gender component visualization is generated at step 610 and placed in the output document. An age tag indicates a desired age condition and may include min and max values, a period, a period qualifier, and units (e.g., min and/or max units). If a min value is present without a max value, the corresponding visualization section in the output document may be in the form of "At least [min] [units] [on start date of/on end date of/during] [period]", as represented, by way of example, by age tag 920 (FIG. 9) and corresponding age visualization section 1020 of the output document (FIG. 10). The selection of start date, end date, or during is based on the presence of a period qualifier indicating the selection (e.g., ON_START_DATE as viewed in FIG. 9). If a max value is present without a min value, the corresponding visualization section in the output document may be of the form "No more than [max] [units] [on start date of/on end date of/during] [period]". If a range is present (indicated by the presence of min and max values), the corresponding section of the output document may be of the form "Between [min] [min units] and [max][max units] [on start date of/on end date of/during] [period]".

A gender tag indicates a desired gender (e.g., male or female), and the corresponding visualization component may indicate the gender for the condition (e.g., "Gender is Female" or "Gender is Male").

When a group tag (e.g., group, logical OR, etc.) is encountered within the identified component section as determined at step 612 (FIG. 6A), the presence of nested sections is determined at step 614. A list component is generated in the output document at step 618 in the absence of nested sections. A decision tree visualization is generated in the output document at step 616 in response to nested sections. The decision tree includes a hierarchical structure with logical operators (e.g., AND, OR, etc.) disposed between hierarchical levels of conditions specified in the measure specification to indicate relationships of those conditions.

For example, the measure specification may contain one or more group tags or sections (e.g., logical OR section 940 including group type section 925 and logical OR sections 920, 960, etc.). The individual group sections (e.g., group type section 925, logical OR sections 930, 960) include a description attribute and corresponding codes for medical or other conditions, and are processed to generate corresponding visualization sections in the output document (e.g., sections 1025, 1030, 1060). The description attribute of a group section provides the descriptions of events for the codes (e.g., displayed in the output document next to checkmarks as illustrated in FIG. 10).

When a logical OR section is encountered, the corresponding visualization section of the output document may include a corresponding text phrase with a listing of the events pertaining to the codes indicated in that section of the measure specification (e.g., as illustrated by sections 925, 930, 960 of the measure specification and corresponding visualization sections 1025, 1030, 1060 of the output document). If a logical AND (not shown) or a logical NOT section (discussed below with respect to FIGS. 17-20) is encountered, the corresponding visualization section of the output document may include a corresponding text phrase with a listing of the events pertaining to the codes indicated in that section of the measure specification. The description attribute of the group section (e.g., logical OR, logical AND, etc.) provides the descriptions of events for the codes (e.g., displayed in the output document next to checkmarks as illustrated in FIG. 10). The logical operator (e.g., OR, AND, etc.) of the group section indicates the relationship of the connected groups in the visualization, while the tag or identifier of the group section that is the parent of the listed codes indicates the corresponding text for the visualization based on the operation in the tag and/or quantity of elements (e.g., "One code indicating the following" (e.g., section 1060 generated from the alternative list of plural elements of section 960; section 1030 generated from the listing of a single element of section 930, etc.), "All codes indicating the following", etc.).

When a group type section (e.g., days with a min days parameter) is encountered, the corresponding visualization section of the output document may be in the form of "One code indicating the following, on at least [min days]" with a listing of the events pertaining to the codes indicated in that section of the measure specification (e.g., as illustrated by section 925 and corresponding visualization section 1025). The description attribute of the group section provides the descriptions of events for the codes (e.g., displayed in the output document next to checkmarks as illustrated in FIG. 10).

Figure 23A:
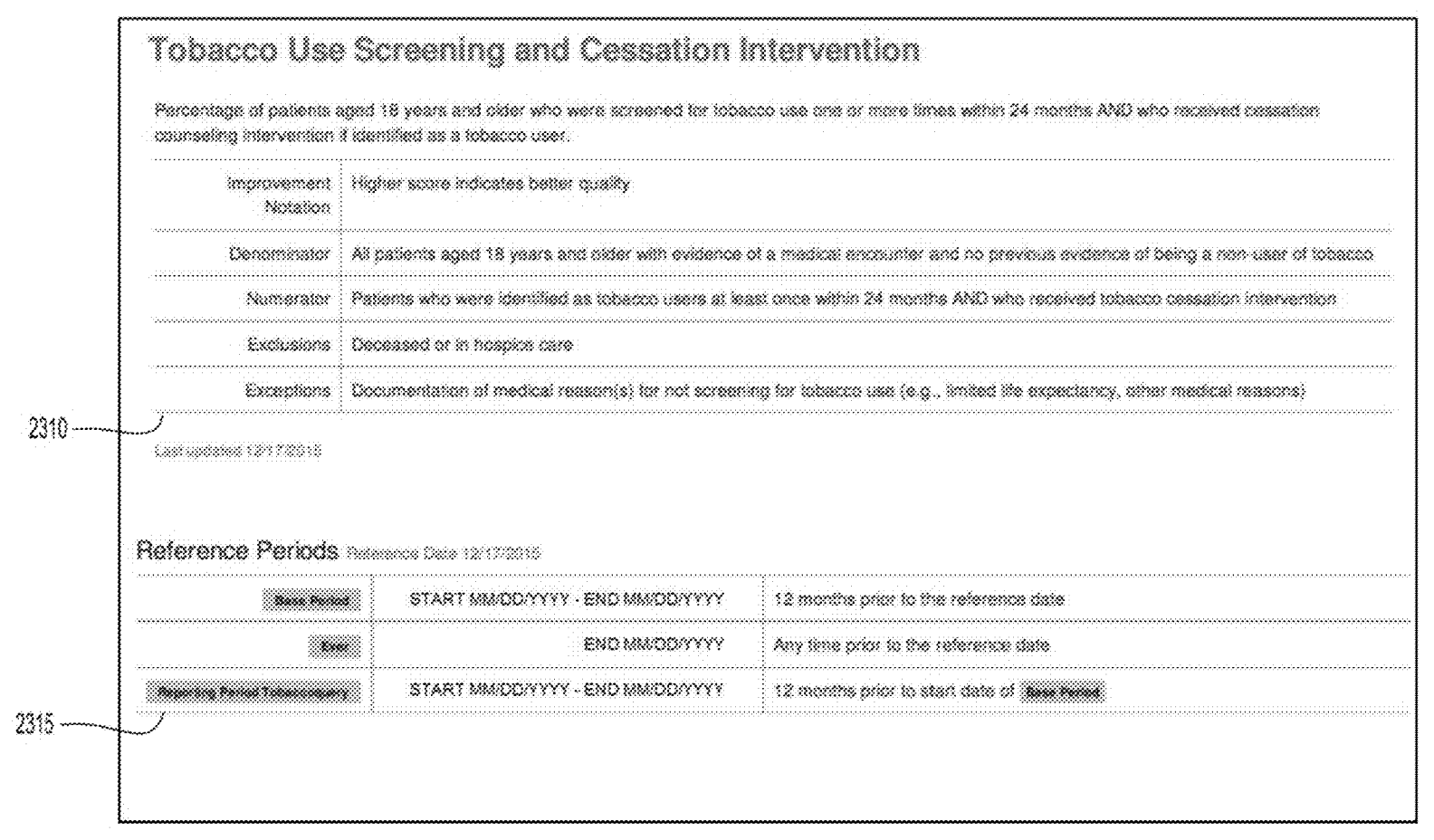
Figure 23B:
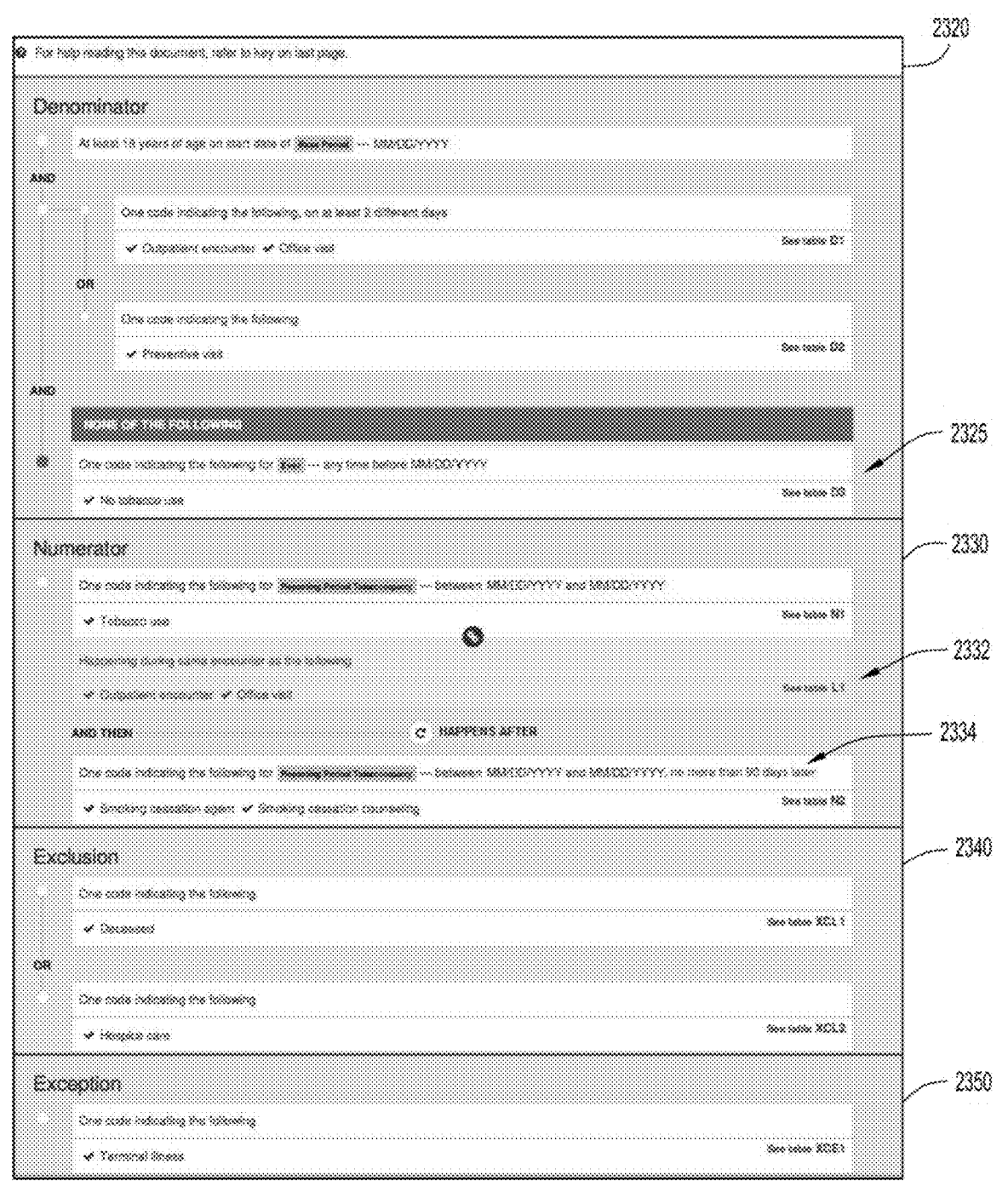

When the group section of the measure specification contains any codes for medical or other conditions (e.g., sections 925, 930), those codes are combined into a table in the output document (e.g., table 1080). Each of the groups is provided with an indicator and placed by the corresponding listing in the output document (e.g., indicator 1070, such as D1, D2, N1, etc.). The numbers for the indicators are generated based on the section of the specification document in which the corresponding group exists, and are listed in the order that the groups appear in the measure specification. If the same group (e.g., having all identical codes) is repeated in the same section of the measure specification, the reference number of the indicator is re-used. The codes in the group are generated in an appendix (e.g., FIG. 23C) at step 620 (FIG. 6A) in the appropriate reference section and separated by type.

When a group section or tag (e.g., group type section, logical OR section, etc.) is nested inside of another group section or tag (e.g., group type section 925 and logical OR section 930 exist inside of another logical OR section 940 in the measure specification), a decision tree is generated in the output document (e.g., decision tree 1055). The decision tree includes a hierarchical structure with logical operators (e.g., AND, OR, etc.) disposed between hierarchical levels of conditions specified in the measure specification to indicate relationships of those conditions. An operator (e.g., AND or OR) is disposed between two or more group sections (or hierarchical levels of the decision tree) (e.g., as illustrated in FIG. 10 between sections 1020, 1040, and 1060 of the output document). When nested group sections occur (e.g., group type section 925 and logical OR section 930 are nested within logical OR section 940), an operator (e.g., AND or OR) is disposed between two or more of the nested group sections (or hierarchical levels of the decision tree) (e.g., as illustrated in FIG. 10 between nested sections 1025, 1030 of section 1040). A logical OR section or tag enables generation of an OR operator in the output document, while a logical AND or NOT section or tag enables generation of an AND operator in the output document.

In the situation where additional group sections and individual codes are nested within another section, both of these are processed separately. For example, a logical AND group includes a logical OR group that contains codes, and additional codes that exist inside of the logical AND group but outside of the internal logical OR group. In this case, two sets of listings are created, where one listing includes the nested group codes, and another listing includes the additional codes. The two listings are separated in the decision tree by the AND operator. A first section in the output document may be of the form "One code indicating the following," and the other section in the output document with the additional codes may be of the form "All codes indicating the following".

Figure 20:
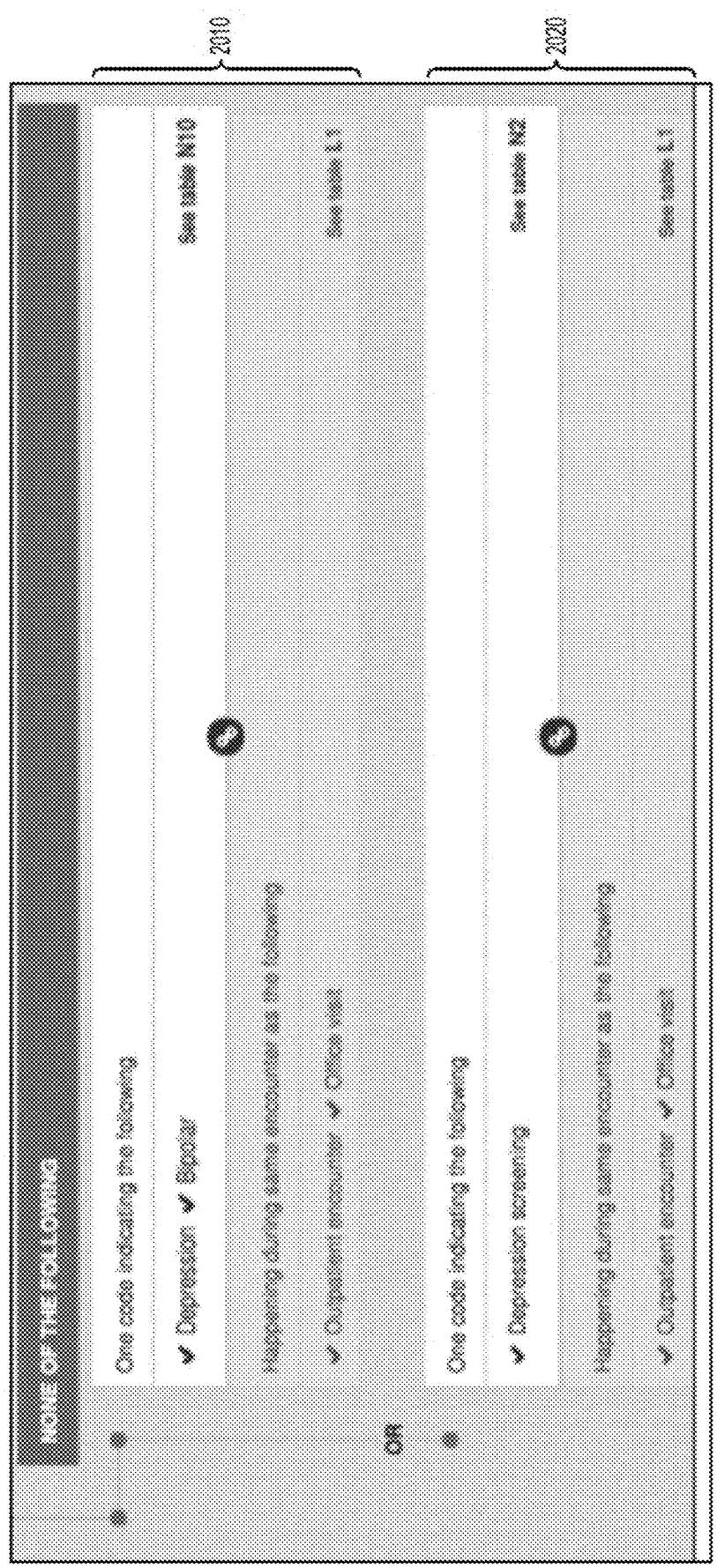
FIG. 20 is a schematic illustration of a visualization from the example portions of the measure specification illustrated in FIG. 19 according to an embodiment of the present invention.

When more complex nesting is present, additional layers of the decision tree are created. In this case, a tag in the measure specification (e.g., cohort tags 915) may function in a similar manner as a logical AND, and an AND operator separates the nested group sections (e.g., sections 920, 940, 960 and corresponding sections of the output document 1020, 1040, 1060). When there is a complex grouping of group sections (e.g., plural nested layers), a bullet list is created in the decision tree of the output document, and the details of the group section and/or operators are provided in substantially the same manner described above in an indented fashion (e.g., FIG. 20, showing an example bullet list). Multiple levels of indentation may be provided due to the quantities of nested groups.

Figure 12:
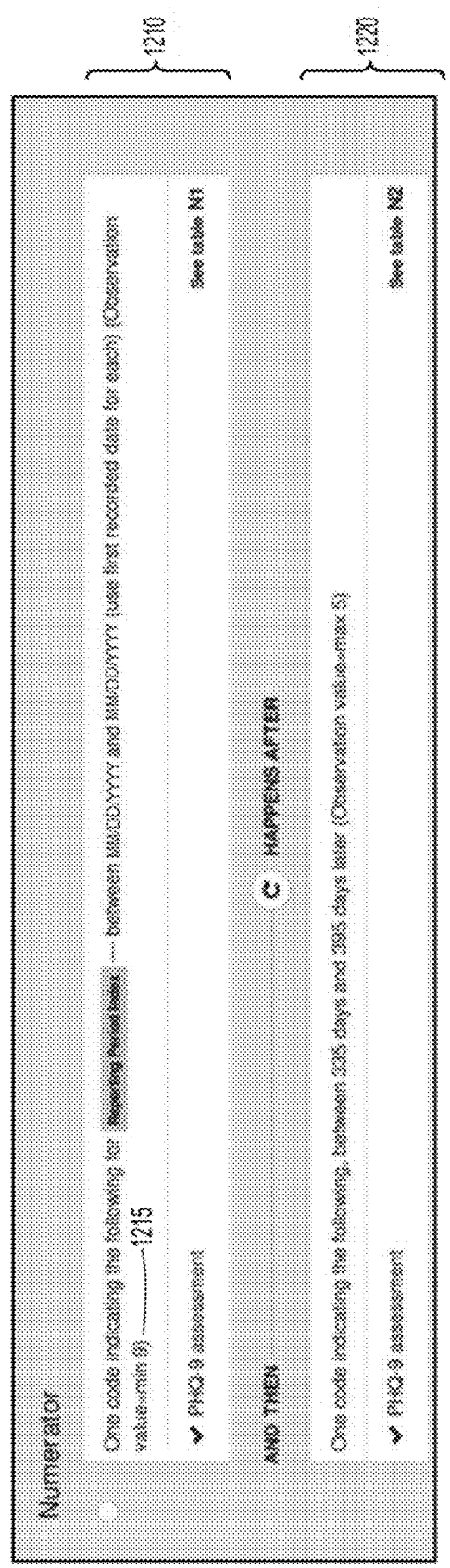
FIG. 12 is a schematic illustration of a visualization from the example portions of the measure specification illustrated in FIG. 11 according to an embodiment of the present invention.

When a temporal sequence is encountered within the identified component section as determined at step 622 (FIG. 6A), a corresponding visualization component is generated at step 624 and placed in the output document. For example, the measure specification may contain a temporal sequence section 1130 (FIG. 11) including an index section 1110 and an event section 1120 that are processed to generate corresponding sections in the output document (e.g., sections 1210, 1220 (FIG. 12)).

A temporal sequence indicates that two or more events must have occurred in a certain order. The index section may include one or more group sections (e.g., logical OR section, group type section, etc.) for an initial event in the temporal sequence that may be processed in substantially the same manner described above (e.g., for FIGS. 9 and 10) to produce corresponding sections in the output document. For example, index section 1110 includes a logical OR section with a min parameter which generates corresponding visualization section 1210 including the form described above (e.g., "One code indicating the following" . . . ). When an index section is encompassed by a date tag (e.g., first date as viewed in FIG. 11), the description may further include "(use first recorded date for each)".

When some other attribute appears on lines of code in a group section (e.g., min parameter 1115 as viewed in FIG. 11), information about that attribute is appended to the end of the description in the output document (e.g., corresponding section 1215 of the output document). If not every code in a group section has that same attribute, or if the group section has different codes with different values, the codes are separated into multiple groups. For example, if two codes in a logical OR section contain a common attribute (e.g., primary=YES), and two codes of that group section do not have that attribute, the codes with the attribute are displayed in the output document in a group along with a description (e.g., "primary=YES"). An OR operator connects that group section to a second group section with the other codes (which does not include that additional description).

The event section provides additional events relative to the events of the index section, and the additional events are displayed in the output document (e.g., section 1220) after the corresponding index section (e.g., section 1210). If no time flow is specified in the temporal sequence section of the measure specification, or if a time flow parameter is set to indicate a prospective temporal sequence (e.g., FORWARD), a divider between the event and index sections of the output document (e.g., a banner that connects the criteria of the index and event sections 1210, 1220 as viewed in FIG. 12) may be of the form "AND THEN—HAPPENS AFTER". If the time flow parameter indicates a prior temporal sequence (e.g., BACKWARD), the divider may be of the form "AND THEN—HAPPENED PREVIOUSLY".

Figure 16:
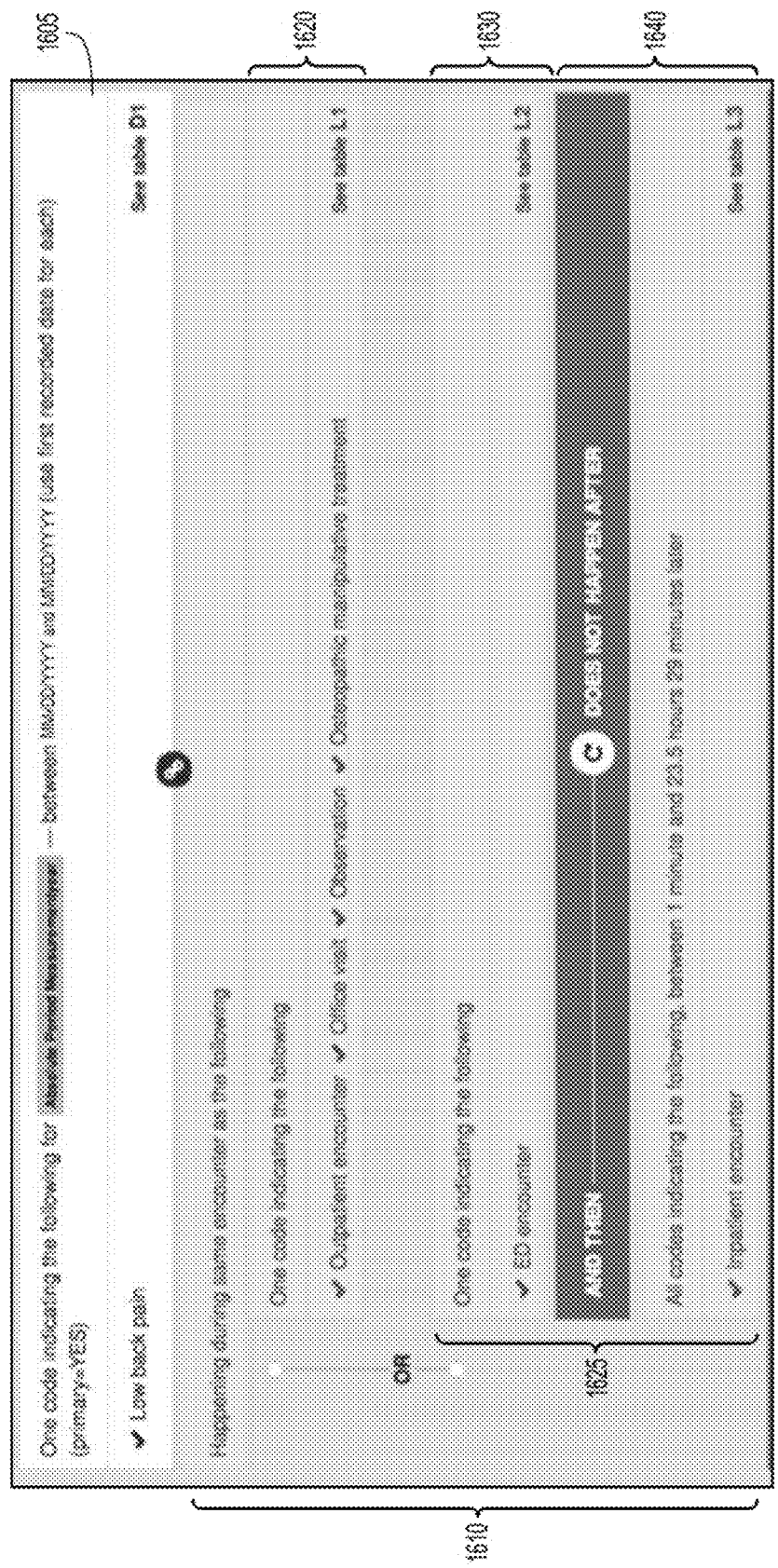
FIG. 16 is a schematic illustration of a visualization from the example portions of the measure specification illustrated in FIG. 15 according to an embodiment of the present invention.
Figure 18:
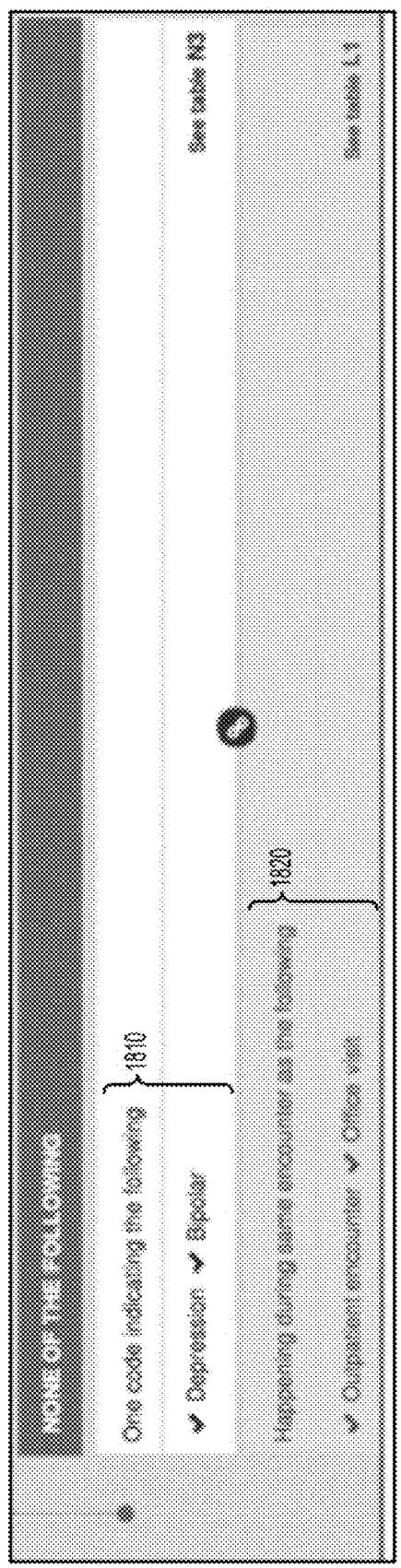
FIG. 18 is a schematic illustration of a visualization from the example portions of the measure specification illustrated in FIG. 17 according to an embodiment of the present invention.

An event section of the measure specification may specify min and max parameters and corresponding units of measurement indicating a timeframe in which the event must have occurred (e.g., section 1120 of FIG. 11 specifying min and max days). If a min parameter is specified without a max parameter in the measure specification, the corresponding section of the output document may be in the form of "at least [min] [min unit] later". If a max parameter is present without and a min parameter in the measure specification, the corresponding section of the output document may be of the form "no more than [max] [max unit] days later". If both parameters are specified in the measure specification, the corresponding section of the output document may be of the form "between [min] [min unit] and [max] [max unit] days later" (e.g., as illustrated by section 1120 and corresponding section 1220 of the output document). When a negate parameter of the event section is set (e.g., negate parameter=TRUE), the divider between the index and event sections in the output document may be red and of the form of "AND THEN—DOES NOT HAPPEN AFTER" (e.g., FIG. 16 shows an example of this divider).

Figure 14:
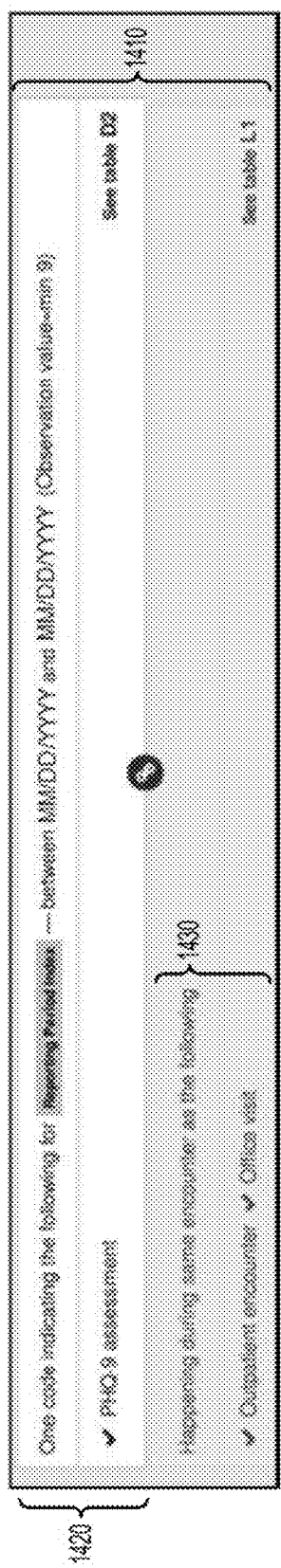
FIG. 14 is a schematic illustration of a visualization from the example portions of the measure specification illustrated in FIG. 13 according to an embodiment of the present invention.

When a linked event is encountered within the identified section as determined at step 626 (FIG. 6A), a corresponding visualization component is generated at step 628 and placed in the output document. For example, the measure specification may contain a link section 1310 (FIG. 13) defining the linkage and another (e.g., logical OR) section 1320 employing the link by a link name parameter 1330 to generate a corresponding section in the output document (e.g., section 1410 (FIG. 14)).

One or more link sections are typically specified at the start of a measure specification, and indicate that some event (e.g., encounter, diagnosis, etc.) must be tied to another event (e.g., happening during the same encounter). There may be multiple links in a measure, and each is assigned a name under a name parameter (e.g., a name parameter 1312 assigning "Outpatient" as viewed in FIG. 13).

When the name of a link is referenced for a code in a group section (e.g., logical OR section, etc.) of the measure specification, a link icon and link filter criteria are appended to a description that may be in the form of "Happening during same encounter as the following" with a listing of the other events from the description in the link section (e.g., section 1330 and corresponding section 1430 of the output document). In the example of FIG. 13, logical OR section 1320 is processed in substantially the same manner described above (e.g., for FIGS. 9 and 10) to produce the corresponding section 1420 of the output document for a logical OR section, while the link provided in section 1330 of the measure specification is processed to produce corresponding section 1430 of the output document.

In the event the link section includes additional complexity, the link criteria are incorporated into the linked event and the above processing is employed to generate the output document. The linked criteria may be shaded to visually differentiate the linked criteria.

For example, the measure specification may contain a link section 1510 (FIG. 15) defining the linkage with a name parameter 1512 assigning the link a name (e.g., "Encounter"). The link section may include a logical OR section 1520 and a temporal sequence section 1525. The temporal sequence section includes an index section 1530 and an event section 1540 with an exclusion (e.g., having a negate parameter set).

By way of example, the name of the link may be referenced for a code in a group section (not shown) relating to back pain to link events to the group section. The measure specification is processed to generate sections for an output document. The initial code group may be a logical OR section that produces corresponding section 1605 (FIG. 16) of the output document.

The link section 1510 is processed to produce corresponding section 1610 of the output document. In particular, logical OR section 1520 may be processed in substantially the same manner described above (e.g., for FIGS. 9 and 10) to produce corresponding section 1620 of the output document (e.g., indicating the listing of descriptions of the codes). Temporal sequence section 1525 of the link section is processed in substantially the same manner described above (e.g., for FIGS. 11 and 12) to produce corresponding section 1625 of the output document. The logical OR and temporal sequence sections are separated by an OR operator in the output document based on the logical OR grouping of these sections in the measure specification. The index section is processed to produce corresponding section 1630 of the output document, while the event section is processed to produce corresponding section 1640 of the output document. The index and event sections are separated by a divider that indicates the event does not happen after the index condition due to the exclusion and setting of the negate parameter in the measure specification as described above.

When a logical NOT tag is encountered within the identified component section as determined at step 630 (FIG. 6B), the presence of a complex or nested construct is determined at step 632. A visualization component is generated at step 634 and placed in the output document for a simple (or non-nested) construct, whereas the visualization component is generated at step 636 to include a listing for a complex or nested construct.

For example, the measure specification may contain a logical NOT section 1710 (FIG. 17) including a logical OR section 1715 with a series of codes 1720. The codes specify a link name to link the event to another event. When a logical NOT section is encountered (e.g., section 1710), the corresponding section of the output document (e.g., section 1810 of FIG. 18) may include a red banner with a description of the form of "NONE OF THE FOLLOWING". Unless there are codes directly within the logical NOT section, rather than just other group sections, this section will have no affect on the description that displays. The linked event of section 1720 of the measure specification is processed to produce corresponding section 1820 of the output document in substantially the same manner described above (e.g., for FIGS. 13-16).

If there is additional complexity (e.g., nesting, etc.) within a logical NOT section, the information is incorporated into the output document and indented relative to the banner, and the corresponding sections of the output document are indicated by a bullet list. For example, the measure specification may include a logical NOT section 1905 (FIG. 19) with a first logical OR section 1910 specifying a link, and a second logical OR section 1920 specifying the same link. The logical NOT section is processed as described above to produce the banner in the output document (FIG. 20). Logical OR section 1910 is processed in substantially the same manner described above (e.g., for FIGS. 9, 10, and 13-16) to produce corresponding section 2010 of the output document specifying a listing of the code descriptions. Section 2010 further includes the linked criteria as described above (e.g., for FIGS. 13-16). Similarly, logical OR section 1920 is processed in substantially the same manner described above (e.g., for FIGS. 9, 10, and 13-16) to produce corresponding section 2020 of the output document specifying a listing of the code descriptions. Section 2020 further includes the linked criteria as described above (e.g., for FIGS. 13-16). An OR operator separates sections 2010 and 2020 of the output document based on the logical OR grouping in the measure specification.

Figure 21:
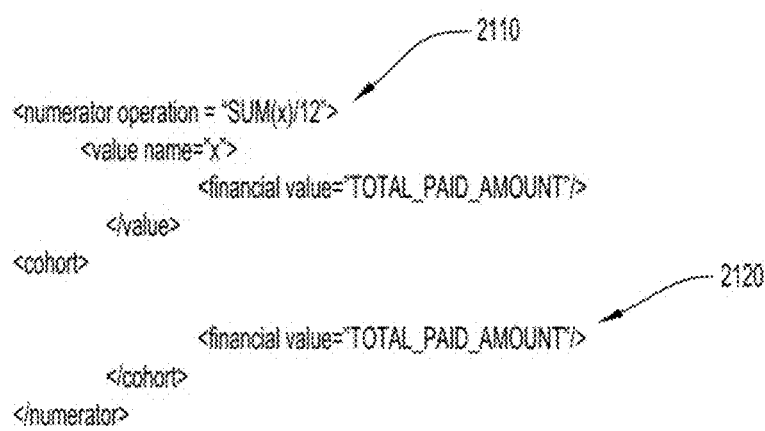
FIG. 21 illustrates example portions of a measure specification in a structured document providing a calculation for the measure according to an embodiment of the present invention.

Some measures may involve financial calculations (e.g., in addition to patient identification). When a calculation tag is encountered within the identified component section of the measure specification as determined at step 638 (FIG. 6B), a corresponding visualization component is generated at step 640 and placed in the output document. For example, the measure specification may contain a calculation section 2110 (FIG. 21) for a numerator specifying a calculation to be performed (e.g., divide a sum or count of instances by 12), and a value section 2120 specifying a value for the calculation. The calculation or operation is typically provided after the section title in the calculation tag.

Figure 22:
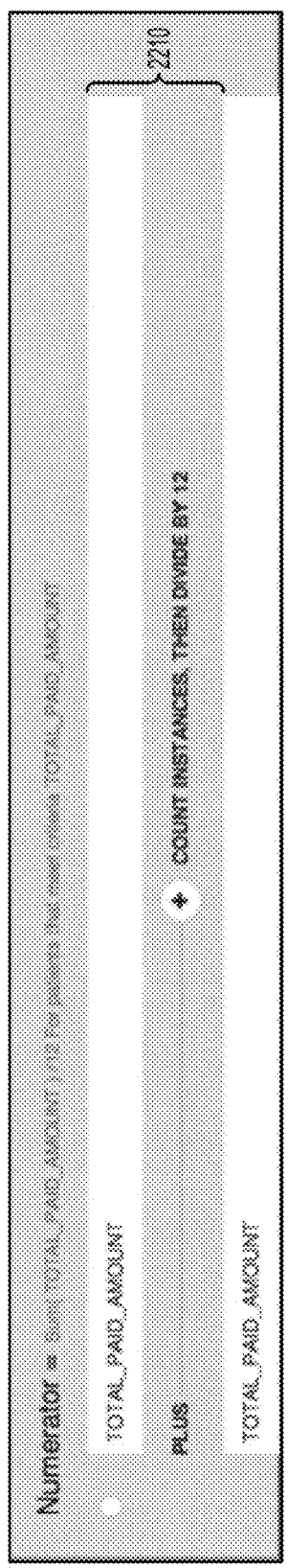
FIG. 22 is a schematic illustration of a visualization from the example portions of the measure specification illustrated in FIG. 21 according to an embodiment of the present invention.

The information in the calculation section is processed to produce a corresponding visualization section in the output document (e.g., sections 2110 and 2120 are processed to produce corresponding section 2210 (FIG. 22) of the output document). For example, section 2210 may include the calculation expression, and the value is provided followed by an expression which may be of the form "AND PLUS— COUNT INSTANCES". In this case, the expression further indicates to divide by 12.

If additional component sections are present in the measure specification as determined at step 642 (FIG. 6B), the additional component sections are identified and processed in substantially the same manner described above to produce corresponding visualization sections for the output document. The component sections may be of any type (e.g., numerator, denominator, exclusion, exception, etc.), and include any quantity of any of the aspect sections described above (e.g., group section, logical OR section, logical AND section, logical NOT section, link section, temporal sequence section, etc.).

Once all of the component sections in the measure specification are processed, the corresponding visualization sections for the output document are assembled to produce a resulting output document at step 644. The output document may be in various electronic formats (e.g., pdf, word processing, spreadsheet, etc.) for storage and/or viewing.

In addition, the output document may be provided (e.g., as a form) on a user interface for validation. A user may interact with the various sections of the output document to modify criteria for the measure. When the output document has been modified as determined at step 646, the sections and/or criteria that have been modified are identified at step 648. Any suitable sections of the measure may be altered through the interface (e.g., numerators, denominators, links, calculations, exclusions, exceptions, etc.). The measure specification (e.g., XML type or other language) is modified based on the identified criteria or sections at step 650. This may be accomplished by changing the various parameters and information in the corresponding sections of the measure specification (e.g., modifying sections of the XML type language, removing sections of the XML type language, adding sections of the XML type language, etc.). The modified measure specification may be executed to validate and produce modified analytics or measures at step 652. This process may be repeated in order to validate and attain a desired operation for the analytic or measure.

Thus, analytic validation module 142 may provide a validation and debugging tool for measures. The validation and debugging tool may present a blank form on the user interface to receive criteria for a measure, and generate the specification document with one or more of the above constructs in a measure specification (e.g., generate code in the XML type or other language). The validation and debugging tool may analyze a measure specification as described above, and present the measure criteria (or output document) (e.g., as a form) on the user interface to enable updating of the measure criteria (e.g., and modifying/removing/adding corresponding sections of the XML type language of the measure specification). The validation and debugging tool may execute the new or updated measure specification (e.g., in batch and/or real-time), and provide results. The updating and executing of the measure specification may be repeated to validate and edit (or refine) the measure specification to correct errors and/or generate a measure producing desired characteristics for a population.

An example output document generated from a measure specification according to an embodiment of the present invention is illustrated in FIGS. 23A-23D. Initially, a measure specification is processed in substantially the same manner described above to produce visualization sections for the output document. The output document includes a measure description section 2310, a reference time period section 2315, a denominator section 2320, a numerator section 2330, an exclusion section 2340, an exception section 2350, an appendix 2360, and a key section 2370.

Measure description section 2310 includes descriptions for the measure, denominator, numerator, exclusions, and exceptions. In addition, this section indicates the magnitude of values providing improvement. The information is extracted from the corresponding information in the measure specification as described above (e.g., for FIGS. 7 and 8).

Reference time period section 2315 includes values for the various time periods within the measure specification (e.g., base period, ever, and absolute period). The time periods are determined from the information in the measure specification as described above (e.g., for FIGS. 7 and 8).

Denominator section 2320 provides the criteria from the measure specification for patients to be included within the measure denominator. This section provides a decision tree showing the relation of criteria via logical operators (e.g., OR, AND, etc.) as described above (e.g., for FIGS. 9 and 10). In this case, the measure specification further includes a logical NOT which is indicated by section 2325 as described above (e.g., for FIGS. 17-20).

Numerator section 2330 provides the criteria from the measure specification for patients to be included within the measure numerator. In this case, the measure specification provided linked events and a temporal sequence which produced corresponding sections 2332 and 2334 as described above (e.g., for FIGS. 11-16).

Exclusion section 2340 provides the criteria from the measure specification for patients to be excluded from the measure. This section, similar to denominator section 2320, provides a decision tree showing the relation of criteria via logical operators (e.g., OR, etc.) as described above (e.g., for FIGS. 9 and 10).

Exception section 2350 provides from the measure specification criteria to be excepted from the numerator and not included in the measure calculation. These excepted patients meet the denominator criteria. This section is produced in substantially the same manner described above (e.g., for FIGS. 9 and 10).

Appendix 2360 includes the tables containing information for the codes within the various sections of the measure specification. This section is produced in substantially the same manner described above (e.g., for FIGS. 9 and 10). Key section 2370 provides explanations for the various notations and symbols in the output document (e.g., reference periods, decision tree operators, linked relationships, temporal relationships, calculation notation, etc.).

It will be appreciated that the embodiments described above and illustrated in the drawings represent only a few of the many ways of implementing embodiments for validating and visualizing performance of analytics.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, analytic validation module, etc.). These systems may include any types of monitors and input devices (e.g., keyboard, mouse, voice recognition, etc.) to enter and/or view information.

It is to be understood that the software (e.g., analytic validation module, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., analytic validation module, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information. The database system may be included within or coupled to the server and/or client systems. The database systems and/or storage structures may be remote from or local to the computer or other processing systems, and may store any desired data.

The present invention embodiments may utilize data in any desired structure (e.g., records, data objects, data structures, etc.), and associate the data with any desired entity (e.g., person, corporate or other business entity, healthcare or other medical related entity, healthcare provider, etc.).

The specifications for the analytics or measures may be within structured or unstructured documents utilizing any types of tags or other identifiers to indicate various constructs or sections (e.g., numerator, denominator, etc.). The specification may employ any suitable language or notation to express criteria for the analytic or measure (e.g., XML, etc.). The arrangement of criteria may be presented within any suitable structure (e.g., decision or other tree, hierarchical or other structure showing relationships, lists, outlines, etc.), and the output document may provide any notations, symbols, expressions, or text arranged in any fashion, and of any color or other visually distinguishing characteristics (e.g., bold, underline, italics or font, font size, etc.) to describe the criteria and/or relationships.

The present invention embodiments may employ any number of any type of user interface (e.g., Graphical User Interface (GUI), command-line, prompt, etc.) for obtaining or providing information (e.g., criteria, analytic results, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The output document may be of any format (e.g., a word processor, spreadsheet, .pdf, image, form for a user or other interface, etc.), include any information arranged in any fashion, and may be configurable based on rules or other criteria to provide desired information to a user (e.g., analytic criteria, results, tables, data sets, etc.).

The present invention embodiments are not limited to the specific tasks or algorithms described above, but may be utilized for analyzing any specification of criteria (e.g., expressed in any language or notation) for an analytic or other action containing criteria or constraints (e.g., measures for registries of healthcare providers, attributions for attributing patients to healthcare providers, etc.).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method of detecting conditions for analytics comprising:

analyzing, via a processor, a structured document including a plurality of sections each specifying a set of conditions in a sequence in a computer language for members of a population in a structured format, wherein the structured document includes logical operators defining an analytic and is executed to perform the analytic on the population;

identifying, via the processor, each section within the structured document and extracting a corresponding set of conditions for that identified section from the computer language in the structured format, wherein the structured document includes a link portion to link events by specifying a link indicating one or more events that occur concurrently with another event;

translating, via the processor, the corresponding extracted set of conditions for each section to a visual presentation of each identified section with a description of the corresponding set of conditions, wherein translating the corresponding extracted set of conditions comprises:

decomposing an extracted set of conditions into individual conditions and logical operators; and generating a tree structure for an identified section to visualize the sequence of the extracted set of conditions from the computer language, wherein the tree structure includes a description of the individual conditions connected by a corresponding logical operator and the one or more concurrent events when the section pertains to a linked event and specifies the link;

modifying, via the processor, the visual presentation to alter the individual conditions and logical operators of at least one identified section to update the analytic to produce desired characteristics for the population;

updating, via the processor, the computer language of the structured document based on the modified visual presentation; and executing, via the processor, the updated structured document to validate results of the updated analytic.

2. The method of claim 1, wherein the set of conditions includes medical conditions.

3. The method of claim 2, wherein individual conditions in the extracted set of conditions for an identified section are temporal, and translating the corresponding extracted set of conditions further comprises:

visually presenting an identified section with descriptions of the individual conditions arranged in an order representing a temporal sequence in the extracted set of conditions.

4. The method of claim 2, wherein the analytic determines a percentage of the population based on a numerator and a denominator, and the plurality of sections includes for the analytic:

a denominator section with corresponding conditions for members of the population to be included in the denominator;

a numerator section with corresponding conditions for members of the population to be included in the numerator;

an exclusion section with corresponding conditions to exclude members of the population from the; and an exception section with corresponding conditions excepted from the numerator.

5. The method of claim 2, further comprising:

visually presenting an appendix section associating extracted sets of conditions to corresponding medical codes.

6. The method of claim 1, wherein the structured document includes an Extensible Markup Language (XML) document.

7. A system for detecting conditions for analytics comprising:

at least one processor configured to:

analyze a structured document including a plurality of sections each specifying a set of conditions in a sequence in a computer language for members of a population in a structured format, wherein the structured document includes logical operators defining an analytic and is executed to perform the analytic on the population;

identify each section within the structured document and extract a corresponding set of conditions for that identified section from the computer language in the structured format, wherein the structured document includes a link portion to link events by specifying a link indicating one or more events that occur concurrently with another event;

translate the corresponding extracted set of conditions for each section to a visual presentation of each identified section with a description of the corresponding set of conditions, wherein translating the corresponding extracted set of conditions comprises:

decomposing an extracted set of conditions into individual conditions and logical operators; and generating a tree structure for an identified section to visualize the sequence of the extracted set of conditions from the computer language, wherein the tree structure includes a description of the individual conditions connected by a corresponding logical operator and the one or more concurrent events when the section pertains to a linked event and specifies the link;

modify the visual presentation to alter the individual conditions and logical operators of at least one identified section to update the analytic to produce desired characteristics for the population;

update the computer language of the structured document based on the modified visual presentation; and execute the updated structured document to validate results of the updated analytic.

8. The system of claim 7, wherein the set of conditions includes medical conditions.

9. The system of claim 8, wherein individual conditions in the extracted set of conditions for an identified section are temporal, and translating the corresponding extracted set of conditions further comprises:

visually presenting an identified section with descriptions of the individual conditions arranged in an order representing a temporal sequence in the extracted set of conditions.

10. The system of claim 8, wherein the analytic determines a percentage of the population based on a numerator and a denominator, and the plurality of sections includes for the analytic:

a denominator section with corresponding conditions for members of the population to be included in the denominator;

a numerator section with corresponding conditions for members of the population to be included in the numerator;

an exclusion section with corresponding conditions to exclude members of the population from the analytic; and an exception section with corresponding conditions excepted from the numerator.

11. The system of claim 8, wherein the at least one processor is further configured to:

visually present an appendix section associating extracted sets of conditions to corresponding medical codes.

12. A computer program product for detecting conditions for analytics, the computer program product comprising a computer readable storage medium having computer readable program code embodied therewith, the computer readable program code executable by at least one processor to cause the at least one processor to:

analyze a structured document including a plurality of sections each specifying a set of conditions in a sequence in a computer language for members of a population in a structured format, wherein the structured document includes logical operators defining an analytic and is executed to perform the analytic on the population;

identify each section within the structured document and extract a corresponding set of conditions for that identified section from the computer language in the structured format, wherein the structured document includes a link portion to link events by specifying a link indicating one or more events that occur concurrently with another event;

translate the corresponding extracted set of conditions for each section to a visual presentation of each identified section with a description of the corresponding set of conditions, wherein translating the corresponding extracted set of conditions comprises:
  decomposing an extracted set of conditions into individual conditions and logical operators; and
  generating a tree structure for an identified section to visualize the sequence of the extracted set of conditions from the computer language, wherein the tree structure includes a description of the individual conditions connected by a corresponding logical operator and the one or more concurrent events when the section pertains to a linked event and specifies the link;

modify the visual presentation to alter the individual conditions and logical operators of at least one identified section to update the analytic to produce desired characteristics for the population;

update the computer language of the structured document based on the modified visual presentation; and execute the updated structured document to validate results of the updated analytic.

13. The computer program product of claim 12, wherein the set of conditions includes medical conditions.

14. The computer program product of claim 13, wherein individual conditions in the extracted set of conditions for an identified section are temporal, and translating the corresponding extracted set of conditions further comprises:
  visually presenting an identified section with descriptions of the individual conditions arranged in an order representing a temporal sequence in the extracted set of conditions.

15. The computer program product of claim 13, wherein the analytic determines a percentage of the population based on a numerator and a denominator, and the plurality of sections includes for the analytic:
  a denominator section with corresponding conditions for members of the population to be included in the denominator;
  a numerator section with corresponding conditions for members of the population to be included in the numerator;
  an exclusion section with corresponding conditions to exclude members of the population from the analytic; and
  an exception section with corresponding conditions excepted from the numerator.

16. The computer program product of claim 13, wherein the computer readable program code further causes the at least one processor to:
  visually present an appendix section associating extracted sets of conditions to corresponding medical codes.

17. The computer program product of claim 12, wherein the structured document includes an Extensible Markup Language (XML) document.

* * * * *